United States Patent [19]
Cozzi et al.

[11] Patent Number: 4,492,707
[45] Date of Patent: Jan. 8, 1985

[54] N-IMIDAZOLYL DERIVATIVES OF 1,2,3,4-TETRAHYDRO-NAPHTHALENE AND INDAN

[75] Inventors: Paolo Cozzi; Antonio Pillan; Pier P. Lovisolo, all of Milan, Italy

[73] Assignee: Farmitalia Carlo Erba S.p.A., Milan, Italy

[21] Appl. No.: 398,545

[22] Filed: Jul. 15, 1982

[30] Foreign Application Priority Data

Jul. 23, 1981 [GB] United Kingdom ............... 8122689
Aug. 5, 1981 [GB] United Kingdom ............... 8123920

[51] Int. Cl.³ ................ A61K 31/415; C07D 233/54
[52] U.S. Cl. ................................ 424/273 R; 548/346
[58] Field of Search ................. 548/346; 424/273 R

[56] References Cited

U.S. PATENT DOCUMENTS

| | | | |
|---|---|---|---|
| 3,485,917 | 12/1969 | Godefroi et al. | 424/273 |
| 4,006,243 | 2/1977 | Strehlke et al. | 424/273 |
| 4,218,461 | 8/1980 | Hoehn | 424/273 |

FOREIGN PATENT DOCUMENTS

| | | |
|---|---|---|
| 1445707 | 8/1976 | United Kingdom . |
| 2071655A | 9/1981 | United Kingdom . |

OTHER PUBLICATIONS

Strehlke, et al., "Antifungale Imidazolverbindungen I", Archiv. der Pharmazie, 308 (1975), pp. 94–109.
Raiskuma, et al., "Synthesis of N-Heteroaromatic Onium Betains of 1,3-Indandione", Chem. Abstracts 89:197464w, (1978).
Neilands, et al., "Synthesis and Properties of the Heterocyclic Onium Betaines of 1,3-Indandione", Chem. Abstracts 87:68100j, (1977).

*Primary Examiner*—Henry R. Jiles
*Assistant Examiner*—Dale A. Bjorkman
*Attorney, Agent, or Firm*—Murray, Whisenhunt and Ferguson

[57] ABSTRACT

Compounds of the formula

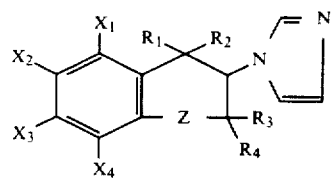

where
Z completes a bond or is a

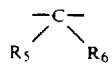

group;
one of $R_1$ and $R_2$ is hydroxy and the other is hydrogen or alkyl, or $R_1$ and $R_2$, taken together, form an oxo group;
and the remaining substituents are as defined in the specification. These compounds possess hypolipaemic properties.

12 Claims, No Drawings

N-IMIDAZOLYL DERIVATIVES OF 1,2,3,4-TETRAHYDRO-NAPHTHALENE AND INDAN

The present invention relates to N-imidazolyl derivatives of 1,2,3,4-tetrahydro-naphthalene, indan and 2-substituted-1-chroman (that is 2-substituted-2,3-dihydro-benzopyran), to a process for their preparation and to pharmaceutical compositions containing them.

The invention provides new compounds having the following general formula (I)

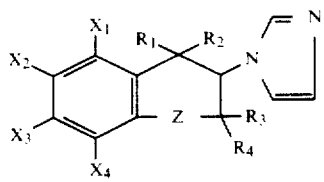

wherein

Z completes a bond, or is an oxygen atom or

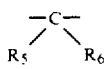

group, wherein each of $R_5$ and $R_6$, being the same or different, is hydrogen or $C_1$-$C_4$ alkyl;

one of $R_1$ and $R_2$ is hydroxy and the other is hydrogen or $C_1$-$C_6$ alkyl, or $R_1$ and $R_2$, taken together, form an oxo group;

one of $R_3$ and $R_4$ is hydrogen or $C_1$-$C_4$ alkyl and the other represents hydrogen or:

(a) $C_1$-$C_8$ alkyl, unsubstituted or substituted by one or more substituents chosen from halogen; hydroxy; cyano; —COOR′, wherein R′ is hydrogen or $C_1$-$C_6$ alkyl;

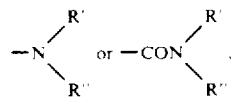

wherein each of R′ and R″, being the same or different, represents hydrogen or $C_1$-$C_6$ alkyl;

(b) phenyl, unsubstituted or substituted by one or more substituents chosen from $C_1$-$C_4$ alkyl; $C_1$-$C_4$ alkoxy; hydroxy; halogen; trihalo-$C_1$-$C_6$ alkyl; cyano; nitro;

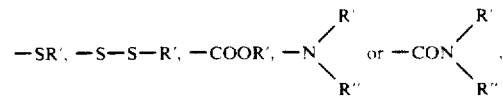

wherein R′ and R″ are as defined above;

(c) a pentatomic or hexatomic heterocyclic ring unsubstituted or substituted by one or more substituents chosen from $C_1$-$C_4$ alkyl; $C_1$-$C_4$ alkoxy; hydroxy; halogen; trihalo-$C_1$-$C_6$ alkyl; cyano; nitro;

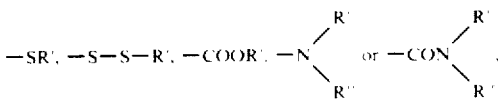

wherein R′ and R″ are as defined above;

(d) straight or branched $C_1$-$C_4$ alkyl or $C_2$-$C_4$ alkenyl, each substituted by a $C_1$-$C_4$ alkyl, a $C_3$-$C_7$ monocycloalkyl, or by a phenyl or heterocyclic ring as defined under (b) and (c) above; or (e) cyano;

wherein R′ and R″ are as defined above;
each of $X_1$, $X_2$, $X_3$ and $X_4$, which may be the same or different, is hydrogen; halogen; hydroxy; nitro; cyano; $C_1$-$C_6$ alkyl; $C_2$-$C_6$ alkenyl; $C_1$-$C_6$ alkoxy; trihalo-$C_1$-$C_6$ alkyl;

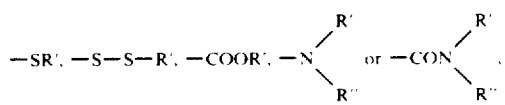

R′ and R″ being as defined above; or a $C_2$-$C_4$ acylamino group; or one of $X_1$, $X_2$, $X_3$ and $X_4$ is phenyl, phenylthio, phenoxy or benzyl, the phenyl, phenylthio, phenoxy and benzyl groups being unsubstituted or substituted by one or more substituents chosen from halogen, $C_1$-$C_6$ alkyl hydroxy, $C_1$-$C_6$ alkoxy, —SR′ or —S—S—R′, wherein R′ is as defined above, and the others are as defined above; or any two adjacent $X_1$, $X_2$, $X_3$ and $X_4$ groups, taken together, complete a saturated or unsaturated 6-membered carbocyclic ring fused to the benzene ring shown in formula (I), the carbocyclic ring being unsubstituted or substituted by one or more substituents selected from halogen, $C_1$-$C_6$ alkyl, halo-$C_1$-$C_6$ alkyl, $C_1$-$C_6$ alkoxy, —SR′ or —S—S—R′, wherein R′ is as defined above, and any groups $X_1$ to $X_4$ not participating in the completion of such a fused ring are as defined above, provided that:

(a) when Z completes a bond or is a —CH$_2$— group, and, at the same time, one of $R_1$ and $R_2$ is hydrogen and the other is hydroxy or $R_1$ and $R_2$, taken together, form an oxo group, then at least one of $R_3$, $R_4$, $X_1$, $X_2$, $X_3$ and $X_4$ is different from hydrogen;

(b) when Z completes a bond or is a —CH$_2$— group, and, at the same time, one of $R_1$ and $R_2$ is hydrogen and the other is hydroxy or $R_1$ and $R_2$, taken together, form an oxo group, one or two of $X_1$, $X_2$, $X_3$ and $X_4$ is halogen, then at least one of the remaining groups of $X_1$, $X_2$, $X_3$ and $X_4$ or at least one of $R_3$ and $R_4$ is other than hydrogen;

(c) when Z is oxygen, at least one of $R_3$ and $R_4$ is other than hydrogen;

(d) when Z is a group

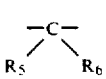

and, at the same time, at least one of $R_3$ and $R_4$ is different from hydrogen, then $R_5$ and $R_6$ are both hydrogen; and (e) when Z is a group

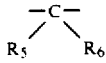

and, at the same time, at least one of $R_5$ and $R_6$ is different from hydrogen, then $R_3$ and $R_4$ are both hydrogen, and the pharmaceutically acceptable salts of the compounds of formula (I).

The present invention also provides pharmaceutical compositions containing a suitable carrier and/or diluent, and, as an active principle, a compound of formula (I), or a pharmaceutically acceptable salt thereof, wherein:

Z completes a bond, or is an oxygen atom or

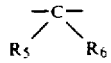

group, wherein each of $R_5$ and $R_6$, being the same or different, is hydrogen or $C_1-C_4$ alkyl;

one of $R_1$ and $R_2$ is hydroxy and the other is hydrogen or $C_1-C_6$ alkyl, or $R_1$ and $R_2$, taken together, form an oxo group;

one of $R_3$ and $R_4$ is hydrogen or $C_1-C_4$ alkyl and the other represents hydrogen or:

(a) $C_1-C_8$ alkyl, unsubstituted or substituted by one or more substituents chosen from halogen; hydroxy; cyano; —COOR', wherein R' is hydrogen or $C_1-C_6$ alkyl;

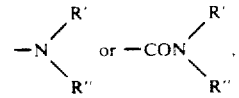

wherein each of R' and R", being the same or different, represents hydrogen or $C_1-C_6$ alkyl;

(b) phenyl, unsubstituted or substituted by one or more substituents chosen from $C_1-C_4$ alkyl; $C_1-C_4$ alkoxy; hydroxy; halogen: trihalo-$C_1-C_6$ alkyl; cyano; nitro;

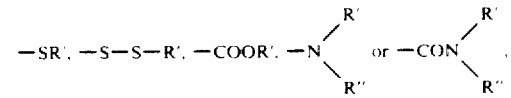

wherein R' and R" are as defined above;

(c) a pentatomic or hexatomic heterocyclic ring unsubstituted or substituted by one or more substituents chosen from $C_1-C_4$ alkyl; $C_1-C_4$ alkoxy; hydroxy; halogen; trihalo-$C_1-C_6$ alkyl; cyano; nitro;

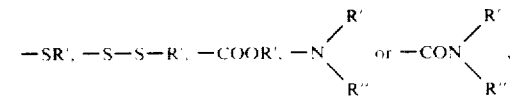

wherein R' and R" are as defined above;

(d) straight or branched $C_1-C_4$ alkyl or $C_2-C_4$ alkenyl, each substituted by a $C_1-C_4$ alkyl, a $C_3-C_7$ monocycloalkyl, or by a phenyl or heterocyclic ring as defined under (b) and (c) above; or (e) cyano;

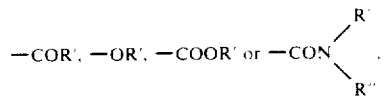

wherein R' and R" are as defined above;
each of $X_1$, $X_2$, $X_3$ and $X_4$, which may be the same or different, is hydrogen; halogen; hydroxy; nitro; cyano; $C_1-C_6$ alkyl; $C_2-C_6$ alkenyl; $C_1-C_6$ alkoxy; trihalo-$C_1-C_6$ alkyl;

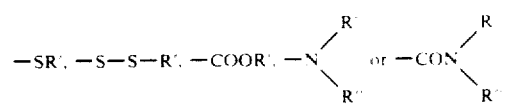

R' and R" being as defined above; or a $C_2-C_4$ acylamino group; or one of $X_1$, $X_2$, $X_3$ and $X_4$ is phenyl, phenylthio, phenoxy or benzyl, the phenyl, phenylthio, phenoxy or benzyl groups being unsubstituted or substituted by one or more substituents chosen from halogen, $C_1-C_6$ alkyl hydroxy, $C_1-C_6$ alkoxy, —SR' or —S—S—R', wherein R' is as defined above, and the others are as defined above; or any two adjacent $X_1$, $X_2$, $X_3$ and $X_4$ groups, taken together, complete a saturated or unsaturated 6-membered carbocyclic ring fused to the benzene ring shown in formula (I), the carbocyclic ring being unsubstituted or substituted by one or more substituents selected from halogen, $C_1-C_6$ alkyl, halo-$C_1-C_6$ alkyl, $C_1-C_6$ alkoxy, —SR' or —S—S—R', wherein R' is as defined above, and any groups $X_1$ to $X_4$ not participating in the completion of such a fused ring are as defined above; provided that:

when Z is an oxygen atom, at least one of $R_3$ and $R_4$ is other than hydrogen;

when Z is a group

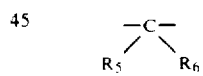

and, at the same time, at least one of $R_3$ and $R_4$ is different from hydrogen, then $R_5$ and $R_6$ are both hydrogen; and when Z is a group

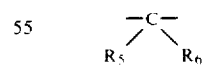

and, at the same time, at least one of $R_5$ and $R_6$ is different from hydrogen, then $R_3$ and $R_4$ are both hydrogen.

The invention also includes within its scope all the possible isomers e.g. cis and trans isomers, stereoisomers and optical isomers and their mixtures, and the metabolites and the metabolic precursors or bioprecursors of the compounds of formula (I).

The numbering used to identify the positions in the compounds of formula (I) is the conventional one, as is depicted in the following Examples:

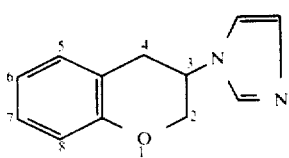

(1)

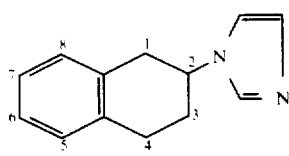

(2)

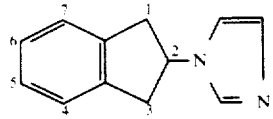

(3)

Pharmaceutically acceptable salts of the compounds of formula (I) include acid addition salts, with inorganic, e.g. nitric, hydrochloric, hydrobromic, sulphuric, perchloric and phosphoric, acids, or organic, e.g. acetic, propionic, glycolic, lactic, oxalic, malonic, malic, maleic, tartaric, fumaric, citric, benzoic, cinnamic, mandelic and salicylic, acids, and salt with inorganic, e.g. alkali metal, especially sodium or potassium, bases or alkaline-earth metal, especially calcium or magnesium, bases, or with organic bases, e.g. alkyl-amines, preferably triethylamine, or tris-(hydroxymethyl)-aminomethane.

The alkyl, alkenyl, alkoxy and alkylthio groups may be branched or straight chain groups.

An alkyl group is preferably methyl, ethyl, propyl, isopropyl or tert. butyl.

An alkoxy group is preferably methoxy, ethoxy or isopropoxy.

An alkylthio group is preferably methylthio, ethylthio or isopropylthio.

A trihalo-$C_1$-$C_6$ alkyl group is, for example, a trihalomethyl group, preferably trifluoro-methyl.

A $C_2$-$C_4$ alkenyl or $C_2$-$C_6$ alkenyl group is preferably vinyl, allyl or 1-propenyl.

A halo-$C_1$-$C_6$ alkyl group is, for example, a halomethyl group, preferably fluoromethyl.

A halogen atom is preferably fluorine, chlorine or bromine.

A pentatomic or hexatomic heterocyclic ring is, for example, thiophene, furane, pyrrole, thiazole, imidazole, pyrazole, thiadiazole, oxazole, isoxazole, pyridine, pyrazine, pyrimidine or pyridazine, preferably thiophene and pyridine.

Any two $X_1$ to $X_4$ can complete a saturated or unsaturated fused ring. The adjacent participating $X_1$ to $X_4$ groups can be $X_2$ and $X_3$, $X_1$ and $X_2$, $X_3$ and $X_4$ or both $X_1$ and $X_2$ and $X_3$ and $X_4$. Each pair of participating $X_1$ to $X_4$ groups has the formula

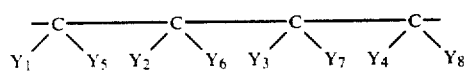

wherein each of the symbols $Y_1$ to $Y_8$, which may be the same or different, represents hydrogen, halogen, $C_1$-$C_6$ alkyl, halo-$C_1$-$C_6$ alkyl, especially trifluoromethyl, $C_1$-$C_6$ alkoxy or SR', R' being as defined above or $Y_5$ and $Y_6$ together and/or $Y_7$ and $Y_8$ together represent a carbon to carbon double bond and the remaining symbols $Y_1$ to $Y_8$ are as defined above. Preferably the pair of participating groups $X_1$ to $X_4$ complete a fused benzene ring unsubstituted or substituted as defined above, preferably by a halogen, preferably chlorine, atom.

Preferred compounds of the invention are the compounds of formula (I), wherein, subject to the above provisos (a), (b), (c), (d) and (e), Z is as defined above;

one of $R_1$ and $R_2$ is hydrogen and the other is hydroxy, or $R_1$ and $R_2$, taken together, form an oxo group;

$R_3$ is hydrogen or methyl;

$R_4$ is (a') hydrogen; (b') $C_1$-$C_3$ alkyl unsubstituted or substituted by halogen, hydroxy; carboxy; (c') phenyl unsubstituted or substituted by halogen or hydroxy; (d') pyridyl or thienyl; or (e') carboxy, alkoxycarbonyl, aminocarbonyl or methoxy;

and wherein $X_1$, $X_2$, $X_3$ and $X_4$ are, independently, hydrogen, halogen, hydroxy, carboxy, trifluoromethyl, $C_1$-$C_4$ alkylthio, $C_1$-$C_4$ alkyl, $C_1$-$C_4$ alkoxy, carbamoyl or

wherein R' and R" are as defined above, or one of $X_1$, $X_2$, $X_3$ and $X_4$ is phenyl, phenylthio, phenoxy or benzyl, the phenyl, phenylthio, phenoxy and benzyl groups being unsubstituted or substituted by halogen, $C_1$-$C_4$ alkyl, $C_1$-$C_4$ alkylthio, hydroxy or $C_1$-$C_4$ alkoxy, and the others are independently, hydrogen, halogen, $C_1$-$C_4$ alkyl, $C_1$-$C_4$ alkylthio or $C_1$-$C_4$ alkoxy, and the pharmaceutically acceptable salts thereof.

More preferred compounds of the invention are the compounds of formula (I), wherein, subject to the above provisos (a), (b) and (c), Z is oxygen or a —$CH_2$— group;

one of $R_1$ and $R_2$ is hydrogen and the other is hydroxy, or $R_1$ and $R_2$, taken together, form an oxo group;

$R_3$ is hydrogen or methyl;

$R_4$ is (a') hydrogen; (b') $C_1$-$C_3$ alkyl unsubstituted or substituted by halogen, hydroxy; carboxy; (c') phenyl unsubstituted or substituted by halogen or hydroxy; (d') pyridyl or thienyl; and wherein $X_1$, $X_2$, $X_3$ and $X_4$ are, independently, hydrogen, halogen, hydroxy, carboxy, trifluoromethyl, $C_1$-$C_4$ alkylthio, $C_1$-$C_4$ alkyl, $C_1$-$C_4$ alkoxy, carbamoyl or

wherein R' and R" are as defined above, or one of $X_1$, $X_2$, $X_3$ and $X_4$ is phenyl, phenylthio, phenoxy or benzyl, the phenyl, phenylthio, phenoxy and benzyl groups being unsubstituted or substituted by halogen, $C_1$-$C_4$ alkyl, $C_1$-$C_4$ alkylthio, hydroxy or $C_1$-$C_4$ alkoxy, and the others are, independently, hydrogen, halogen, $C_1$-$C_4$alkyl, $C_1$-$C_4$alkylthio or $C_1$-$C_4$alkoxy, and the pharmaceutically acceptable salts thereof.

Examples of preferred compounds of the invention or, respectively, of active ingredients of the pharmaceutical compositions of the invention are the following:

(1) 2-methyl-3-(1-imidazolyl)-2,3-dihydro-4H-1-benzopyran-4-one;
(2) 2-methyl-3-(1-imidazolyl)-2,3-dihydro-5-methoxy-4H-1-benzopyran-4-one;
(3) 2-methyl-3-(1-imidazolyl)-2,3-dihydro-6-methoxy-4H-1-benzopyran-4-one;
(4) 2-methyl-3-(1-imidazolyl)-2,3-dihydro-7-methoxy-4H-1-benzopyran-4-one;
(5) 2-methyl-3-(1-imidazolyl)-2,3-dihydro-5-hydroxy-4H-1-benzopyran-4-one;
(6) 2-methyl-3-(1-imidazolyl)-2,3-dihydro-6-hydroxy-4H-1-benzopyran-4-one;
(7) 2-methyl-3-(1-imidazolyl)-2,3-dihydro-7-hydroxy-4H-1-benzopyran-4-one;
(8) 2-methyl-3-(1-imidazolyl)-2,3-dihydro-6,8-dibromo-7-hydroxy-4H-1-benzopyran-4-one;
(9) 2-methyl-3-(1-imidazolyl)-2,3-dihydro-6-tert.butyl-7-hydroxy-4H-1-benzopyran-4-one;
(10) 2-methyl-3-(1-imidazolyl)-2,3-dihydro-5-hydroxy-6,8-di-tert.butyl-4H-1-benzopyran-4-one;
(11) 2-methyl-3-(1-imidazolyl)-2,3-dihydro-6-bromo-7-hydroxy-4H-1-benzopyran-4-one;
(12) 2-methyl-3-(1-imidazolyl)-2,3-dihydro-6-carboxy-4H-1-benzopyran-4-one;
(13) 2-methyl-3-(1-imidazolyl)-2,3-dihydro-6-carboxy-8-bromo-4H-1-benzopyran-4-one;
(14) 2-methyl-3-(1-imidazolyl)-2,3-dihydro-6-ethoxycarbonyl-8-bromo-4H-1-benzopyran-4-one;
(15) 2-methyl-3-(1-imidazolyl)-2,3-dihydro-6-n.propyl-7-hydroxy-4H-1-benzopyran-4-one;
(16) 2-methyl-3-(1-imidazolyl)-2,3-dihydro-6-[(4-hydroxy)-phenyl]-4H-1-benzopyran-4-one;
(17) 2-methyl-3-(1-imidazolyl)-2,3-dihydro-6-bromo-7-methoxy-4H-1-benzopyran-4-one;
(18) 2-n.propyl-3-(1-imidazolyl)-2,3-dihydro-4H-1-benzopyran-4-one;
(19) 2-n.propyl-3-(1-imidazolyl)-2,3-dihydro-6-carboxy-4H-1-benzopyran-4-one;
(20) 2-phenyl-3-(1-imidazolyl)-2,3-dihydro-4H-1-benzopyran-4-one;
(21) 2-phenyl-3-(1-imidazolyl)-2,3-dihydro-6-carboxy-4H-1-benzopyran-4-one;
(22) 2-[(3,4-dihydroxy)-phenyl]-3-(1-imidazolyl)-2,3-dihydro-5,7-dihydroxy-4H-1-benzopyran-4-one;
(23) 2-(3-pyridyl)-3-(1-imidazolyl)-2,3-dihydro-4H-1-benzopyran-4-one;
(24) 2-(4-pyridyl)-3-(1-imidazolyl)-2,3-dihydro-7-hydroxy-4H-1-benzopyran-4-one;
(25) 2,2-dimethyl-3-(1-imidazolyl)-2,3-dihydro-6-tert.butyl-7-hydroxy-4H-1-benzopyran-4-one;
(26) 2,2-dimethyl-3-(1-imidazolyl)-2,3-dihydro-4H-1-benzopyran-4-one;
(27) 2-methyl-3-(1-imidazolyl)-2,3-dihydro-4H-1-benzopyran-4-ol;
(28) 2-methyl-3-(1-imidazolyl)-2,3-dihydro-6,8-dibromo-7-hydroxy-4H-1-benzopyran-4-ol;
(29) 2-methyl-3-(1-imidazolyl)-2,3-dihydro-6-tert.butyl-7-hydroxy-4H-1-benzopyran-4-ol;
(30) 2-methyl-3-(1-imidazolyl)-2,3-dihydro-6-carboxy-4H-1-benzopyran-4-ol;
(31) 2-methyl-3-(1-imidazolyl)-2,3-dihydro-6-bromo-7-hydroxy-4H-1-benzopyran-4-ol;
(32) 2-phenyl-3-(1-imidazolyl)-2,3-dihydro-6-carboxy-4H-1-benzopyran-4-ol;
(33) 2-[(3,4-dihydroxy)]-phenyl-3-(1-imidazolyl)-2,3-dihydro-5,7-dihydroxy-4H-1-benzopyran-4-ol;
(34) 2-(1-imidazolyl)-3,4-dihydro-7-amino-1(2H)-naphthalenone;
(35) 2-(1-imidazolyl)-3,4-dihydro-7-dimethylamino-1(2H)-naphthalenone;
(36) 2-(1-imidazolyl)-3,4-dihydro-7-acetylamino-(1(2H)-naphthalenone;
(37) 2-(1-imidazolyl)-3,4-dihydro-7-methoxy-1(2H)-naphthalenone;
(38) 2-(1-imidazolyl)-3,4-dihydro-8-methoxy-1(2H)-naphthalenone;
(39) 2-(1-imidazolyl)-3,4-dihydro-5-bromo-6-hydroxy-1(2H)-naphthalenone;
(40) 2-(1-imidazolyl)-3,4-dihydro-5-bromo-6-methoxy-1(2H)-naphthalenone;
(41) 2-(1-imidazolyl)-3,4-dihydro-6-hydroxy-7-tert.butyl-1(2H)-naphthalenone;
(42) 2-(1-imidazolyl)-3,4-dihydro-5,7-dibromo-6-hydroxy-1(2H)-naphthalenone;
(43) 2-(1-imidazolyl)-3,4-dihydro-7-carboxy-1(2H)-naphthalenone;
(44) 2-(1-imidazolyl)-3,4-dihydro-5-bromo-7-carboxy-1(2H)-naphthalenone;
(45) 2-(1-imidazolyl)-3,4-dihydro-8-carboxy-1(2H)-naphthalenone;
(46) 2-(1-imidazolyl)-3,4-dihydro-7-methoxy-8-bromo-1(2H)-naphthalenone;
(47) 2-(1-imidazolyl)-3,4-dihydro-7-hydroxy-8-bromo-1(2H)-naphthalenone;
(48) 2-(1-imidazolyl)-3,4-dihydro-5-allyl-6-hydroxy-1(2H)-naphthalenone;
(49) 2-(1-imidazolyl)-3,4-dihydro-7-phenyl-1(2H)-naphthalenone;
(50) 2-(1-imidazolyl)-3,4-dihydro-3-methyl-1(2H)-naphthalenone;
(51) 2-(1-imidazolyl)-3,4-dihydro-3-phenyl-7-carboxy-1(2H)-naphthalenone;
(52) 2-(1-imidazolyl)-3,4-dihydro-3-carboxy-1(3H)-naphthalenone;
(53) 2-(1-imidazolyl)-1,2,3,4-tetrahydro-7-methoxy-1-naphthalenol;
(54) 2-(1-imidazolyl)-1,2,3,4-tetrahydro-7-carboxy-1-naphthalenol;
(55) 2-(1-imidazolyl)-1,2,3,4-tetrahydro-6-hydroxy-7-tert.butyl-1-naphthalenol;
(56) 2-(1-imidazolyl)-1,2,3,4-tetrahydro-5-bromo-6-hydroxy-1-naphthalenol;
(57) 2-(1-imidazolyl)-1,2,3,4-tetrahydro-8-carboxy-1-naphthalenol;
(58) 2-(1-imidazolyl)-5-methoxy-1-indanone;
(59) 2-(1-imidazolyl)-6-carboxy-1-indanone; and
(60) 2-(1-imidazolyl)-3-methyl-1-indanone,
and the pharmaceutically acceptable salts thereof.

The above-numbered compounds (1) to (33), (53) to (57) and (60) may be both in the form of cis or trans isomers and of their mixtures.

The structural formulae of the above-numbered compounds, indicated according to their progressive number, are reported in the following Table:

| Compound | $X_1$ | $X_2$ | $X_3$ | $X_4$ | Z | $R_1, R_2$ | $R_3$ | $R_4$ |
|---|---|---|---|---|---|---|---|---|
| 1 | H | H | H | H | —O— | =O | H | $CH_3$ |
| 2 | $OCH_3$ | H | H | H | —O— | =O | H | $CH_3$ |
| 3 | H | $OCH_3$ | H | H | —O— | =O | H | $CH_3$ |

-continued

| Compound | X₁ | X₂ | X₃ | X₄ | Z | R₁, R₂ | | R₃ | R₄ |
|---|---|---|---|---|---|---|---|---|---|
| 4 | H | H | OCH₃ | H | —O— | =O | | H | CH₃ |
| 5 | OH | H | H | H | —O— | =O | | H | CH₃ |
| 6 | H | OH | H | H | —O— | =O | | H | CH₃ |
| 7 | H | H | OH | H | —O— | =O | | H | CH₃ |
| 8 | H | Br | OH | Br | —O— | =O | | H | CH₃ |
| 9 | H | t.Bu | OH | H | —O— | =O | | H | CH₃ |
| 10 | OH | t.Bu | H | t.Bu | —O— | =O | | H | CH₃ |
| 11 | H | Br | OH | H | —O— | =O | | H | CH₃ |
| 12 | H | COOH | H | H | —O— | =O | | H | CH₃ |
| 13 | H | COOH | H | Br | —O— | =O | | H | CH₃ |
| 14 | H | COOEt | H | Br | —O— | =O | | H | CH₃ |
| 15 | H | n.Pr | OH | H | —O— | =O | | H | CH₃ |
| 16 | H | Ph(4OH) | H | H | —O— | =O | | H | CH₃ |
| 17 | H | Br | OCH₃ | H | —O— | =O | | H | CH₃ |
| 18 | H | H | H | H | —O— | =O | | H | n.Pr |
| 19 | H | COOH | H | H | —O— | =O | | H | n.Pr |
| 20 | H | H | H | H | —O— | =O | | H | Ph |
| 21 | H | COOH | H | H | —O— | =O | | H | Ph |
| 22 | OH | H | OH | H | —O— | =O | | H | Ph(3,4OH) |
| 23 | H | H | H | H | —O— | =O | | H | 3-Py |
| 24 | H | H | OH | H | —O— | =O | | H | 4-Py |
| 25 | H | t.Bu | OH | H | —O— | =O | | CH₃ | CH₃ |
| 26 | H | H | H | H | —O— | =O | | CH₃ | CH₃ |
| 27 | H | H | H | H | —O— | OH | H | H | CH₃ |
| 28 | H | Br | OH | Br | —O— | OH | H | H | CH₃ |
| 29 | H | t.Bu | OH | H | —O— | OH | H | H | CH₃ |
| 30 | H | COOH | H | H | —O— | OH | H | H | CH₃ |
| 31 | H | Br | OH | H | —O— | OH | H | H | CH₃ |
| 32 | H | COOH | H | H | —O— | OH | H | H | Ph |
| 33 | OH | H | OH | H | —O— | OH | H | H | Ph(3,4OH) |
| 34 | H | NH₂ | H | H | —CH₂— | =O | | H | H |
| 35 | H | N(CH₃)CH₃ | H | H | —CH₂— | =O | | H | H |
| 36 | H | CH₃CONH | H | H | —CH₂— | =O | | H | H |
| 37 | H | OCH₃ | H | H | —CH₂— | =O | | H | H |
| 38 | OCH₃ | H | H | H | —CH₂— | =O | | H | H |
| 39 | H | H | OH | Br | —CH₂— | =O | | H | H |
| 40 | H | H | OCH₃ | Br | —CH₂— | =O | | H | H |
| 41 | H | t.Bu | OH | H | —CH₂— | =O | | H | H |
| 42 | H | Br | OH | Br | —CH₂ | =O | | H | H |
| 43 | H | COOH | H | H | —CH₂— | =O | | H | H |
| 44 | H | COOH | H | Br | —CH₂— | =O | | H | H |
| 45 | COOH | H | H | H | —CH₂— | =O | | H | H |
| 46 | Br | OCH₃ | H | H | —CH₂— | =O | | H | H |
| 47 | Br | OH | H | H | —CH₂— | =O | | H | H |
| 48 | H | H | OH | allyl | —CH₂— | =O | | H | H |
| 49 | H | Ph | H | H | —CH₂— | =O | | H | H |
| 50 | H | H | H | H | —CH₂— | =O | | H | CH₃ |
| 51 | H | COOH | H | H | —CH₂— | =O | | H | Ph |
| 52 | H | H | H | H | —CH₂— | =O | | H | COOH |
| 53 | H | OCH₃ | H | H | —CH₂— | OH | H | H | H |
| 54 | H | COOH | H | H | —CH₂— | OH | H | H | H |
| 55 | H | t.Bu | OH | H | —CH₂— | OH | H | H | H |
| 56 | H | H | OH | Br | —CH₂— | OH | H | H | H |
| 57 | COOH | H | H | H | —CH₂— | OH | H | H | H |
| 58 | H | H | OCH₃ | H | direct linkage | =O | | H | H |
| 59 | H | COOH | H | H | direct linkage | =O | | H | H |
| 60 | H | H | H | H | direct linkage | =O | | H | CH₃ |

The abbreviations n.Pr, t.Bu, Ph and Py mean respectively n.propyl, tert.butyl, phenyl and pyridyl.

The compounds of formula (I) can be prepared by a process comprising:

(A) reacting a compound of formula (II), or a reactive derivative thereof

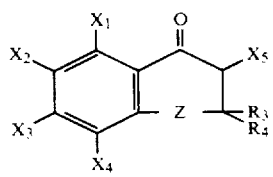

(II)

wherein $X_1$, $X_2$, $X_3$, $X_4$, $R_3$, $R_4$ and Z are as defined above and $X_5$ is halogen or an active ester group, with imidazole or a salt thereof, thus obtaining a compound having formula (I), wherein $R_1$ and $R_2$, taken together, form an oxo group; or (B) cyclizing a compound of formula (III)

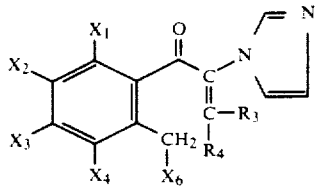
(III)

wherein $X_1$, $X_2$, $X_3$, $X_4$ and $R_3$ are as defined above, $R_4$ is as defined above except hydroxy and $C_1$-$C_6$ alkoxy, and $X_6$ is a halogen atom, thus obtaining a compound of formula (I), wherein $R_1$ and $R_2$, taken together, form an oxo group, $R_4$ is as defined above except hydroxy and $C_1$-$C_6$ alkoxy, and Z is the group

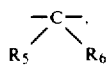

wherein $R_5$ and $R_6$ are both hydrogen; or (c) reacting a compound of formula (IV)

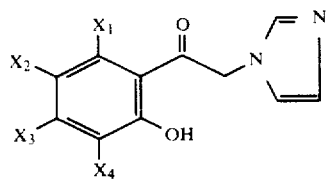
(IV)

wherein $X_1$, $X_2$, $X_3$ and $X_4$ are as defined above, with a compound of formula (V)

$R_3$—CO—$R_4$ (V)

wherein $R_3$ and $R_4$ are as defined above, or a reactive derivative thereof, thus obtaining a compound of formula (I), wherein $R_1$ and $R_2$, taken together, form are oxo group and Z represents an oxygen atom; or (D) reducing a compound of formula (VI)

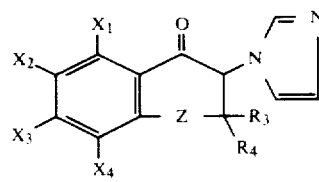
(VI)

wherein $X_1$, $X_2$, $X_3$, $X_4$, $R_3$, $R_4$ and Z are as defined above, thus obtaining a compound of formula (I) wherein one of $R_1$ and $R_2$ is hydrogen and the other is hydroxy; or (E) reacting a compound of formula (VI), as defined above, with a compound of formula (VII)

$R_7$—M (VII)

wherein M is Li or the group MgX, in which X is halogen, and $R_7$ is $C_1$-$C_6$ alkyl, thus giving a compound of formula (I), wherein one of $R_1$ and $R_2$ is hydroxy and the other is $C_1$-$C_6$ alkyl; and, if desired, converting a compound of formula (I) into another compound of formula (I), and/or removing a protective group, and/or, if desired, converting a compound of formula (I) into a pharmaceutically acceptable salt thereof and/or, if desired, converting a salt into a free compound and/or, if desired, separating a mixture of isomers of formula (I) into the single isomers.

The above provisos (a) and (b) exclude from the invention compounds of formula (I) which are already known in literature: Archiv. der Pharmazie: 308, 94–109, (1975) and U.K. Pat. No. 1,445,707, without any reference, however, either to a possible therapeutical use or to a possible pharmaceutical formulation containing these compounds.

The above proviso (c) excludes from the invention compounds of formula (I) which are already known from published British patent application No. 2071655A.

The compounds of formula (I), excluded from the invention by the above provisos (d) and (e), have been excluded owing to reasons of sterical hindrance.

A reactive derivative of a compound of formula (II) may be a compound of formula (II) wherein the carbonyl group is protected before the reaction with imidazole, or a salt thereof, and then deprotected at the end of the reaction, by following, e.g., known procedures.

The carbonyl group may be protected for example in the form of a ketale group of formula

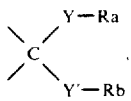

in which Y and Y', independently, are oxygen or sulphur and each of Ra and Rb, whether the same or different, is $C_1$-$C_6$ alkyl, or Ra and Rb, taken together, form a straight or branched $C_2$-$C_6$ alkylene chain. The carbonyl group is preferably protected in the form of 1,3-dioxolan group.

When in a compound of formula (II) $X_5$ is a halogen atom, it is preferably chlorine or bromine and when it is an active ester group, it is preferably —O-tosyl or —O-mesyl.

A salt of imidazole is preferably an alkali metal, e.g. sodium or potassium, salt or a silver salt.

The reaction of a compound of formula (II), or a reactive derivative thereof, with imidazole or a salt thereof is preferably carried out either (a) in the absence of solvent, at a temperature preferably ranging about between the room temperature and 180° C. and for reaction times which may vary from some minutes to about 20 hours using, if necessary, an excess of imidazole or a salt thereof, or (b) in the presence of a suitable solvent, preferably dimethylformamide, dimethylacetamide, hexamethylphosphorotriamide benzene, toluene, ethyl acetate, ethyl alcohol, dioxane or acetone, at a temperature preferably ranging between about 0° C. and the reflux temperature, for reaction times varying from some minutes to about 12 hours and using, if necessary, an excess of imidazole or a stoichiometric amount of a tertiary base, preferably triethylamine.

When in a compound of formula (III) $X_6$ is a halogen atom, it is preferably chlorine or bromine.

The cyclization of a compound of formula (III) may be performed with an alkaline-earth metal, e.g. calcium or magnesium, preferably magnesium, and, if desired, in the presence of cuprous salts e.g. halides, e.g., hydrochloride or hydrobromide, or acetate in catalytic or stoichiometric amounts, in a suitable solvent, e.g. a $C_1$-$C_6$ alkyl ether, preferably diethyl ether or methylethyl ether, tetrahydrofurane, dioxane, benzene, toluene or a mixture thereof, at temperatures ranging from about 0° C. to about 100° C., for reaction times varying from about 1 up to about 8 hours.

The reaction of a compound of formula (IV) with a compound of formula (V) or a reactive derivative thereof, which may be, for instance, a bisulphite addition compound may be performed by using a suitable solvent, e.g. water, methyl or ethyl alcohol or acetic acid, or mixtures of these solvents with water or if desired using as solvent an excess of compound (V), at a temperature preferably ranging between about the room temperature and the reflux temperature for reaction times varying from few minutes to some hours. In the case that the compound of formula (V) is formaldehyde, $R_3$ and $R_4$ being both hydrogen, a preferred reactive derivative of a compound of formula (V) may be paraformaldehyde or trioxymethylene.

The reduction of a compound of formula (VI) may be, for example, performed (a) by treatment with an alkali metal borohydride, e.g. $NaBH_4$, in a suitable solvent, e.g. methyl or ethyl alcohol or a mixture of water and ethyl alcohol, or (b) by treatment with $LiAlH_4$ in an anhydrous solvent, e.g. diethyl ether or tetrahydrofuran, at a temperature ranging, in both cases, preferably between 0° C. and the reflux temperature, for reaction times varying approximately from 1 to 6 hours.

Alternatively the reduction of a compound of formula (VI) may be carried out by catalytic hydrogenation in the presence of a suitable catalyst, e.g. palladium, platinum, $PtO_2$, ruthenium or Raney-nickel in a suitable solvent, preferably chosen from methyl alcohol, ethyl alcohol, acetic acid, cyclohexane, n-hexane, ethyl acetate, benzene or toluene and operating at a pressure ranging from atmospheric pressure to about 50 atmospheres and at a temperature ranging from about 20° C. to about 100° C.

When in the compounds of formula (VI) one or more substituents are reducible groups, e.g.

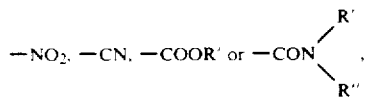

the reduction is preferably performed with an alkali metal borohydride, preferably $NaBH_4$, in order to avoid the simultaneous reduction of such reducible groups.

When in the compound of formula (VII) M is —MgX, in the Grignard reagent of formula $R_7MgX$, X is preferably iodine or bromine.

The reaction of a compound of formula (VI) with a compound of formula $R_7MgX$ may be performed in an anhydrous suitable solvent, preferably an ether, conveniently anhydrous diethyl ether, and at temperatures ranging from about 0° C. to the room temperature.

The reaction of a compound of formula (VI) with a compound of formula (VII) wherein M is Li, that is a lithium-alkyl of formula $LiR_7$, wherein $R_7$ is as defined above, may be carried out, for example, in a suitable anhydrous solvent, which may be, for instance, n-hexane or n-pentane, at a temperature ranging from about −60° C. to about −80° C., preferably at approximately −78° C.

A compound of formula (I) may be converted, if desired, into another compound of formula (I).

These optional conversions may be carried out by methods known in themselves.

Thus, for example, a compound of formula (I) wherein one or more of $X_1$, $X_2$, $X_3$ and $X_4$ is hydrogen may be converted into a compound of formula (I) wherein one or more of $X_1$, $X_2$, $X_3$ and $X_4$ is a halogen atom, e.g. chlorine or bromine, by reaction with chlorine or bromine in the presence of a Friedel-Crafts catalyst, preferably $AlCl_3$, operating in a suitable solvent, e.g. $CH_2Cl_2$.

A compound of formula (I) wherein one or more of $R_3$, $R_4$, $X_1$, $X_2$, $X_3$, and $X_4$ is a $C_1$-$C_6$ alkoxy group may be converted into a compound of formula (I) wherein one or more of $R_3$, $R_4$, $X_1$, $X_2$, $X_3$ and $X_4$ is a hydroxy group by following conventional procedures well known in organic chemistry. For example by treatment with a strong mineral acid, i.e. HCl, HBr, HI, preferably HBr, at temperature ranging from 30° C. to the reflux temperature, preferably at reflux temperature, or by treatment with a Lewis acid, for example $AlCl_3$ or $BF_3$, in a suitable solvent, i.e. $CH_2Cl_2$ or nitrobenzene, at temperature ranging from the room temperature to 80° C.

A compound of formula (I), wherein one or more of $X_1$, $X_2$, $X_3$ and $X_4$ is a $C_2$-$C_4$ acylamino group may be converted into another compound of formula (I), wherein one or more of $X_1$, $X_2$, $X_3$ and $X_4$ is an amino group, by following conventional procedures. The reaction may be carried out in a suitable protic solvent, e.g. water, lower aliphatic alcohol, or mixtures thereof, by treatment with strong mineral acids, e.g. hydrochloric, hydrobromic or sulphuric acid, at a temperature ranging from room temperature to the reflux temperature.

A compound of formula (I), wherein one or more of $X_1$, $X_2$, $X_3$ and $X_4$ is amino, may be converted into another compound of formula (I), wherein one or more of $X_1$, $X_2$, $X_3$ and $X_4$ is —NH$C_1$-$C_6$ alkyl or —N($C_1$-$C_6$ alkyl)$_2$ by following known methods. For instance a compound of formula (I), wherein one or more of $X_1$, $X_2$, $X_3$ and $X_4$ is amino may be converted into another compound of formula (I), wherein one or more of $X_1$, $X_2$, $X_3$ and $X_4$ is —N($C_1$-$C_6$ alkyl)$_2$ by reaction with a suitable $C_1$-$C_6$ alkyl halide, preferably iodide or bromide, in the presence of a suitable basic agent, preferably a tertiary amine, e.g. triethylamine, in a solvent, e.g. chosen from, water, lower aliphatic alcohol, benzene, toluene, dioxane or a mixture thereof, at a temperature ranging from about 60° C. to the reflux temperature.

A compound of formula (I) wherein one or more of $R_3$, $R_4$, $X_1$, $X_2$, $X_3$ and $X_4$ is an esterified carboxy group may be converted into a compound of formula (I) wherein one or more of $R_3$, $R_4$, $X_1$, $X_2$, $X_3$ and $X_4$ is a free carboxy group, by hydrolysis, e.g. acid hydrolysis, in a solvent, such as water or a lower aliphatic alcohol, operating at a temperature ranging from the room temperature to about 150° C.

A compound of formula (I), wherein one or more of $R_3$, $R_4$, $X_1$, $X_2$, $X_3$ and $X_4$ is —$CONH_2$, may be converted into a compound of formula (I), where one or more of $R_3$, $R_4$, $X_1$, $X_2$, $X_3$, and $X_4$ is a free carboxy group, by hydrolysis, preferably by acid hydrolysis, in a suitable solvent, such as water, or by the Bouveault procedure, that is by treatment with NaNO₂ and an aqueous strong inorganic acid, i.e. H₂SO₄, operating at temperatures ranging from the room temperature and 100° C.

A compound of formula (I) wherein one or more of R₃, R₄, X₁, X₂, X₃ and X₄ is a free carboxy group may be converted into a compound of formula (I) wherein one or more of R₃, R₄, X₁, X₂, X₃ and X₄ is an esterified carboxy group, i.e., an alkoxycarbonyl group, by reaction, for example, of the alkali metal salt of the acid with a suitable alkyl halide, in an inert solvent, such as acetone, dioxane, dimethylformamide, hexamethylphosphorotriamide, at a temperature ranging from about 0° C. to about 100° C.

A compound of formula (I), wherein one or more of R₃, R₄, R₅, R₆, X₁, X₂, X₃ and X₄ is hydrogen may be converted into a compound of formula (I) where one or more of R₃, R₄, R₅, R₆, X₁, X₂, X₃ and X₄ is C₁-C₆ alkyl, by alkylation through a Friedel-Crafts reaction, that is by reaction with a C₁-C₆ alkylhalide, preferably chloride, bromide or iodide, or with a C₁-C₆ alcohol in a suitable solvent, e.g. nitrobenzene or CH₂Cl₂, or CS₂, the former in the presence of appropriate amount of a Friedel-Crafts catalyst, such as AlCl₃, ZnCl₂ or BF₃, the latter in the presence of a strong mineral acid as HF, HClO₄ or, if desired, in concentrated H₂SO₄ or in concentrated H₃PO₄ without additional solvent, at temperatures ranging from the room temperature to 100° C.

Also the optional salification of a compound of formula (I) as well as the conversion of a salt into the free compound and the separation of a mixture of isomers into the single isomers may be carried out by conventional methods.

For example the separation of a mixture of geometric isomers, e.g. cis- and trans-isomers, may be carried out by fractional crystallization from a suitable solvent or by chromatography; either column chromatography or high pressure liquid chromatography.

A compound of formula (II) in which X₅ is a halogen atom may be obtained halogenating the corresponding compound of formula (VIII)

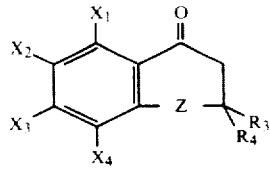

wherein X₁, X₂, X₃, X₄, R₃, R₄ and Z are defined above.

The halogenation of a compound of formula (VIII) to give a compound of formula (II) is usually carried out with a stoichiometric amount of halogen, preferably bromine or chlorine, in a suitable solvent, e.g. diethyl ether, methylene chloride; CHCl₃, CCl₄, CS₂ or acetic acid, at a temperature ranging from about 0° C. to about 100° C., for reaction times ranging approximately between 3 and 12 hours.

Alternatively, the halogenation reaction of a compound of formula (VIII) may be carried out by using a stoichiometric amount of sulphuryl chloride in a suitable solvent, e.g. methylene chloride, chloroform or benzene or using two equivalents of CuBr₂ in a suitable solvent e.g. ethyl acetate, chloroform, or methylenechloride, at temperatures ranging from the room to the reflux temperature, for reaction times ranging from 3 to 12 hours.

The halo-derivatives of formula (II) can be also obtained using conventional methods known in the art where the compounds of formula (VIII) are converted, for example, by treatment, in the presence of p-toluenesulphonic acid as catalyst, with isopropenyl acetate or a convenient anhydride of a fatty acid, in their corresponding enol acetates or enol esters and then the obtained masked carbonyl compounds are reacted with halogens in the presence of an organic or inorganic base.

Similarly, halo-compounds of formula (II) are obtained when a compound of formula (VIII) is converted into an enol ether or into an enol silyl ether, with methods which are known in the art, and the obtained compound is treated with a halogenating agent chosen, e.g., from halogens, N-halo-amides, N-halo-imides and CuBr₂.

A compound of formula (II) wherein X₅ is an active ester group such as, e.g., —O-tosyl or —O-mesyl, may be obtained by reacting the corresponding alcohol [which is known or may be prepared by known methods[, e.g. with a p-toluene-sulphonyl or methanesulphonyl halide, preferably the chloride.

The reaction is preferably carried out in an anhydrous inert solvent, e.g. acetone, at temperatures ranging about from the room to the reflux temperature.

A compound of formula (III) may be obtained by reacting a compound of formula (IX)

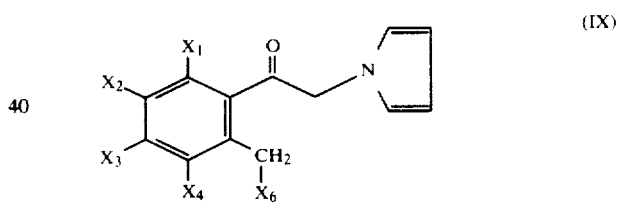

wherein X₁, X₂, X₃, X₄, and X₆ are as defined above, with a compound of formula (X)

wherein R₃ is as defined above and R₄ is as defined above except hydroxy and C₁-C₆ alkoxy.

The reaction between a compound of formula (IX) and a compound of formula (X) may be carried out by following well known methods, for example the reaction may be performed in a suitable organic solvent, e.g. diethyl ether, tetrahydrofurane, ethyl acetate or CH₂Cl₂ and, if desired, in the presence of a base, preferably a secondary amine, i.e. piperidine or diethylamine, at temperatures ranging from about 0° C. to the reflux temperature of the solvent.

A compound of formula (IV) may be obtained by reacting a compound of formula (XI)

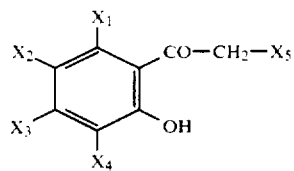

wherein $X_1$, $X_2$, $X_3$, $X_4$ and $X_5$ are as defined above, with imidazole or a salt thereof, preferably an alkali metal, e.g. a sodium or potassium salt, or a silver salt.

The reaction may be carried out by using the same reaction conditions reported above for the reaction between a compound of formula (II) and imidazole or a salt thereof.

The compounds of formula (V) are known compounds.

The compounds of formula (VI) are compounds covered by the general formula (I), wherein $R_1$ and $R_2$, taken together, form an oxo group.

The compounds of formula (VII) are known compounds.

The compounds of formula (VIII) are known compounds or they may be prepared by known methods from known compounds. For instance a compound of formula (VIII) may be prepared by cyclizing a compound of formula (XII)

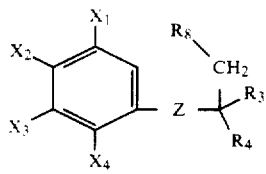

wherein $X_1$, $X_2$, $X_3$, $X_4$, $R_3$, $R_4$ and $Z$ are as defined above and $R_8$ is cyano, carboxy, $C_1$-$C_7$ alkoxycarbonyl or the group —$COX_6$, wherein $X_6$, being as defined above, is, preferably, chlorine or bromine.

The cyclization of a compound of formula (XII) in which $R_8$ is cyano, carboxy or $C_1$-$C_7$ alkoxy-carbonyl, may be carried out by treatment with a suitable cyclizing agent, e.g. phosphoric anhydride, polyphosphoric acid, chlorosulphonic acid or sulphuric acid, optionally in the presence of a suitable solvent, preferably chosen from benzene, toluene and xylene, at a temperature which may range from about 20° C. to about 130° C. The cyclization of a compound with formula (XII) wherein $R_8$ is the group —$COX_6$ and $X_6$ is as defined above, is preferably carried out by using $AlCl_3$ in the presence of a suitable solvent, e.g. carbon disulfide, methylene chloride or carbon tetrachloride, at temperatures ranging from about 0° C. to about 50° C.

A compound of formula (IX) may be prepared by halogenating a compound of formula (XIII)

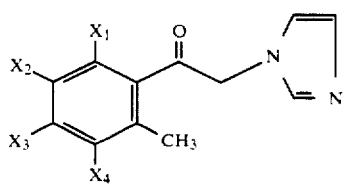

wherein $X_1$, $X_2$, $X_3$ and $X_4$ are as defined above.

The reaction may be carried out by using a suitable halogenating agent, i.e. N-bromosuccinimide (NBS) or N-chlorosuccinimide (NCS), and by following usual procedures. For example the reaction may be performed in a polar solvent, e.g. $CCl_4$, at temperatures varying from the room temperature to the reflux temperature and, optionally, by adding a suitable amount of benzoylperoxide as radical initiator.

If desired, the carbonyl group in a compound of formula (XIII) may be protected before the reaction takes place and then removed at the end of the reaction by following known methods. The carbonyl group may be protected for example in the form of a group of formula

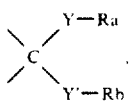

in which Y and Y', independently, are oxygen or sulphur and each of $R_a$ and $R_b$, whether the same or different, is $C_1$-$C_6$ alkyl or $R_a$ and $R_b$, taken together, form a straight or branched $C_2$-$C_6$ alkylene chain. The carbonyl group is preferably protected in the form of a 1,3-dioxolan group and the reaction may be performed by following well known procedures, e.g. by reacting a compound of formula (XIII) with diethyleneglycol in the presence of a strong inorganic or organic acid, i.e. p.toluenesulphonic acid, to give the corresponding 1,3-dioxolan, i.e. 1,2-ethylenedioxy, derivative. As stated above the procting group, after the halogenating reaction, is removed by following usual procedures, e.g. by treatment with diluted aqueous inorganic acids.

The compounds of formula (X) are known compounds.

The compounds of formula (XI) are known or they may be prepared by known methods from known compounds, for instance by halogenating compounds of formula (XIV)

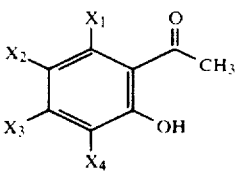

wherein $X_1$, $X_2$, $X_3$ and $X_4$ are as defined above, using the same reagents and reaction conditions reported above for the halogenation of compounds of formula (VIII).

The compounds of formula (XII) are known compounds.

A compound of formula (XIII) may be prepared by reacting a compound of formula (XV)

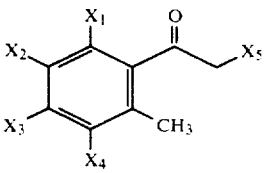

wherein $X_1$, $X_2$, $X_3$, $X_4$ and $X_5$ are as defined above, with imidazole or a salt thereof and by following the same reaction conditions reported above between a compound of formula (II) and imidazole or a salt thereof.

The compounds of formula (XIV) and (XV) are known compounds or may be prepared by known methods from known compounds. When in the compounds having formulae (I), (II), (III), (IV), (VI), (VIII), (IX), (XI), (XII), (XIII), (XIV) an (XV) groups are present which need to be protected during the reactions reported above, e.g. amino, hydroxy, further carboxy groups, etc., such groups can be protected in a conventional way before the reaction takes place.

Examples of protecting groups are those usually employed in the synthesis of peptides. For example, to protect amino groups, acetyl, benzoyl, tert.butoxy-carbonyl, p-methoxy-benzyloxy-carbonyl, o-nitro-phenyl-sulphonyl, dichloroacetyl protective groups may be employed. To protect hydroxy groups acetyl, benzoyl, benzyloxy, tetrahydropyranyl, β-methoxy-ethoxymethyl (MEM) or trialkylsilyl, as tert.butyl-dimethylsilyl groups may be, for instance, employed. To protect the carboxy group, tert.butyl, benzhydryl and p-methoxy-benzyl groups may be employed.

The protecting groups are then removed, at the end of the reaction, in a known manner, e.g. by mild acid hydrolysis or by mild catalytic reduction, for example with Pd/C as catalyst at atmospheric pressure.

The compounds and the pharmaceutical compositions of the invention are active in lowering cholesterol and triglycerides, in increasing the total serum HDL cholesterol, as well as in increasing the ratio between α-lipoprotein and β-liproprotein total cholesterol. [As is known, drugs selective increasing the HDL-cholesterol concentration in blood and/or the ratio between α and β lipoprotein cholesterol are useful in prevention and therapy of atherosclerosis: Glueck C. J., Artery, 2, 196 (1976); Day C. E. in Frank-H-Clarke (Ed.) Annual reports in Medicinal Chemistry, 13, 184, Chapter 20- Academic Press, N.Y. 1978].

The activity of the compounds, for example 2-(1-imidazolyl)-3,4-dihydro-5-bromo-6-hydroxy-1(2H)-naphthalenone, and the pharmaceutical compositions of the invention, was evaluated, e.g., on groups of OFA: Ico: SD (IoPS-Caw) male rats fed for six days with hypercholesterolaemic diet according to C. E. Day [Schurr P. E., Schultz H. R., Day C. E. (Eds) Atherosclerosis and drug discovery-Plenum Pub. Corp., 217 (1976)].

The compounds were suspended in "Methocel$^R$" (methylcellulose, a 0.5% solution in water) and administered by stomach tube at the dose of 50 mg/kg for 4 days.

Groups of animals were treated with the suspending agent only (control groups).

The total serum cholesterol was determined with the method of Allain, Clin. Chem., 20, 470, 1974.

The total serum HDL cholesterol was determined according to Demacker P.N.M. [Clin. Chem., 23, 1238 (1977)].

The total β-lipoprotein cholesterol was determined by difference between total serum cholesterol and HDL cholesterol.

Statistical analysis was performed by the Student's test for independent samples.

In the animals treated with hypercholesterolaemic diet the tested compounds were found to decrease the total serum cholesterol, to increase the total serum HDL cholesterol and the ratio between α- and β-lipoprotein total cholesterol.

The compounds and the pharmaceutical compositions of the invention, are also endowed with blood platelet-antiagregating activity. This activity was evaluated, for example for 2-(1-imidazolyl)-3,4-dihydro-7-methoxy-1(2H)-naphthalenone, e.g. "in vitro" on the basis of the ability of the test compounds to inhibit the collagen-induced platelet aggregation in Guinea pig platelet rich plasma according to the method of Born [Born G. V. R.-Nature, 1942, 927 (1962)].

In view of their elevated lipid lowering activity, of their action on HDL cholesterol and in view of their platelet antiaggregation activity the compounds and the pharmaceutical compositions of the invention, are useful in the treatment of dislipidaemies and of the atherosclerotic syndrome and in the prevention and treatment of syndromes caused by platelet aggregation disorders, such as thrombosis.

The toxicity of the compounds of the invention and of the active ingredients of the pharmaceutical compositions of the invention, was found to be quite negligible and therefore they can be safely used in therapy. The evaluation of the toxicity (as orientative acute toxicity, i.e. $LD_{50}$), was carried out, e.g., as follows: nine hours food deprived mice were treated orally with single administration of increasing doses, then housed and normally fed; the $LD_{50}$ was assessed on the seventh day after the treatment.

For example, as indicative datum the $LD_{50}$ of the compound 2-(1-imidazolyl)-3,4-dihydro-5-bromo-6-hydroxy-1(2H)-naphthalenone was found $>800$ mg/kg body weight.

In the treatment of dislipidaemies the compounds of the invention and the active ingredients of the pharmaceutical compositions of the invention, can be administered in a variety of dosage forms, e.g. orally, in the form of tablets, capsules, sugar or film coated tablets, liquid solutions or suspensions, rectally, in the form of suppositories, parentally, e.g. intramuscularly, or by intravenous injection or infusion, in the form of aerosols or creams, powders or lotions for topical use.

The dosage depends on the age, weight, conditions of the patient and administration route; for example the dosage adopted for oral administration to adult humans ranges from about 50 to about 200 mg pro dose, from 1 to 3 times daily, preferably from 50 to 100 mg pro dose 1–3 times a day.

The pharmaceutical compositions of the invention are usually prepared following conventional methods and are administered in a pharmaceutically suitable form. For example, the solid oral forms may contain, together with the active compound, diluents, e.g., lactose, dextrose, saccharose, cellulose, corn starch and potato starch, lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinyl pyrrolidone, disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, such as, sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile isotonic water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The I.R. spectrum of the compounds was measured in solid phase (KBr) or Nujol solution or in a solution of a suitable solvent such as CHCl$_3$, using Perkin-Elmer 125 spectrophotometer.

The N.M.R. spectrum was measured preferably in solution of dimethyl sulphoxide-d$_6$ or of CDCl$_3$, using a 90 M-hertz Bruker HFX apparatus.

The R$_f$ values were determined by thin layer chromatography on ready-to-use silica gel plates of 0.25 mm coating thickness.

The following examples illustrate but do not limit the invention.

EXAMPLE 1

A solution of 2-hydroxy-α-(1-imidazolyl)-acetophenone (6.5 g), acetaldehyde (20 ml) and acetic acid (400 ml) was heated at 100° C. for 10 hours.

The solvent was evaporated under reduced pressure and the residue, taken up with CH$_2$Cl$_2$ (100 ml), washed with H$_2$O, was extracted with a solution of 8% HCl.

The acid solution, neutralized with NaHCO$_3$, extracted with CH$_2$Cl$_2$, dried and evaporated, gave 6 g of trans-2-methyl-3-(1-imidazolyl)-2,3-dihydro-4H-1-benzopyran-4-one; m.p.=144°–146° C.;

Analysis of the elements: Found: C 67.34; H 5.33; N 11.90 Theoretical for C$_{13}$H$_{12}$N$_2$O$_2$: C 68.4; H 5.25; N 12.26; T.L.C.: eluent: CH$_2$Cl$_2$: MeOH=180:20 R$_f$=0.4; N.M.R. (CDCl$_3$) δ p.p.m. 1.37 (3H d —C$\underline{H}_3$) 4.50–4.98 (2H m

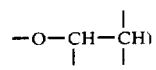

7.02 (1H broad s

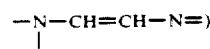

7.11 (2H m

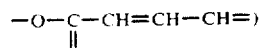

7.23 (1H broad s

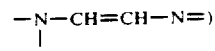

7.58 (1H broad s

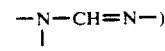

7.62 (1H dd

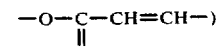

7.95 (1H dd

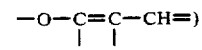

J

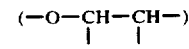

≃12 Hz 2-hydroxy-α-(1-imidazolyl)-acetophenone used above was prepared as follows:

a solution of 2-hydroxy-α-bromo-acetophenone (7 g), imidazole (6 g) and N,N-dimethylformamide (50 ml), was heated to 40° C. for 2 hours. The solution was poured into ice-water, the solid was filtered off and taken up with NaOH. The basic solution, washed with CHCl$_3$, neutralized with HCl, extracted with CHCl$_3$, dried and evaporated to dryness gave 6 g of the above product, m.p. 156°–158° C.;

Analysis of the elements: Found: C 65.19; H 4.97; N 13.65 Theoretical for C$_{11}$H$_{10}$N$_2$O$_2$: C 65.2; H 4.94; N 13.85; T.L.C.=eluent: CH$_2$Cl$_2$:MeOH=180:20 R$_f$=0.2.

By analogous procedure, starting from the appropriate 2-hydroxy-α-(1-imidazolyl)-acetophenones and the appropriate aldehydes, the following compounds were prepared:

trans-2-n.propyl-3-(1-imidazolyl)-2,3-dihydro-4H-1-benzopyran-4 one;

Analysis of the elements: Found: C 68.74; H 6.41; N 10.25 Theoretical for C$_{15}$H$_{16}$N$_2$O$_2$: C 70.29; H 6.28; N 10.92; T.L.C.: eluent CH$_2$Cl$_2$:MeOH=180:20 R$_f$=0.6; N.M.R. (CDCl$_3$) δ p.p.m. 0.92 (3H t —C$\underline{H}_3$) 1.2–1.8 (4H m —C$\underline{H}_2$—C$\underline{H}_2$—) 4.65 (1H m

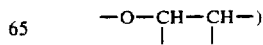

4.93 (1H d 6.90 (1H broad s $$-O-CH-CH-)$$
$$\phantom{-O-}|\phantom{CH-}|$$

7.0–7.2 (2H m $$-N-CH=CH-N=)$$
$$\phantom{-N-}|$$

7.12 (1H broad s $$-O-C-CH=CH-CH=)$$
$$\phantom{-O-}\|$$

7.57 (1H broad s $$-N-CH=CH-N=)$$
$$\phantom{-N-}|$$

7.59 (1H m $$-N-CH=N-)$$
$$\phantom{-N-}|$$

7.93 (1H dd $$-O-C-CH=CH-CH=)$$
$$\phantom{-O-}\|$$

J $$(-O-CH-CH-)$$
$$\phantom{(-O-}|\phantom{CH-}|$$

≃12 Hz;
2-methyl-3-(1-imidazolyl)-2,3-dihydro-6,8-dibromo-7-hydroxy-4H-1-benzopyran-4 one; m.p. 245° C. (dec);
Analysis of the elements: Found: C 38.24; H 2.57; N 6.63; Br 38.7 Theoretical for $C_{13}H_{10}Br_2N_2O_3$: C 38.84; H 2.50; N 6.97 Br 39.75; T.L.C. = eluent: $CH_2Cl_2$:MeOH = 180:20 $R_f$ = 0.25; N.M.R. ($CF_3COOD$) δ p.p.m. 1.42; 1.65 (3H 2d —CH$_3$ cis and trans) 5.20 (1H m $$-O-CH-CH-)$$
$$\phantom{-O-}|\phantom{CH-}|$$

5.60; 6.38 (1H 2d $$-O-CH-CH-$$
$$\phantom{-O-}|\phantom{CH-}|$$

trans and cis) 7.60; 7.78 (2H broad s $$-N-CH=CH-N=)$$
$$\phantom{-N-}|$$

8.21; 8.29 (1H 2 s $$-N-CH=N-)$$
$$\phantom{-N-}|$$

trans and cis) 9.00; 9.36 (1H broad s $$-N-CH=CH-N=)$$
$$\phantom{-N-}|$$

J $$(-O-CH-CH- \text{ trans})$$
$$\phantom{(-O-}|\phantom{CH-}|$$

≃12 Hz
J $$(-O-CH-CH- \text{ cis})$$
$$\phantom{(-O-}|\phantom{CH-}|$$

≃4 Hz;
trans-2-methyl-3-(1-imidazolyl)-2,3-dihydro-5-methoxy-4H-1-benzopyran-4-one; m.p. = 145°–149° C.;
Analysis of the elements: Found: C 64.8; H 5.34; N 10.68 Theoretical for $C_{14}H_{14}N_2O_3$: C 65.10; H 5.46; N 10.85; T.L.C. eluent: AcOEt:EtOH = 170:30 $R_f$ ≃ 0.27; N.M.R. ($CDCl_3$) δ p.p.m.: 1.32 (3H, d, $$-CH-CH_3)$$
$$\phantom{-}|$$

3.89 (3H, s, —O—CH$_3$) 4.56–4.80 (2H, m, $$-O-CH-CH-)$$
$$\phantom{-O-}|\phantom{CH-}|$$

6.53–7.51 (6H, m, aromatics + imidazole);
trans-2-methyl-3-(1-imidazolyl)-2,3-dihydro-7-methoxy-4H-1-benzopyran-4-one; m.p. = 130° C. (dec.);
Analysis of the elements: Found: C 64.97; H 5.25; N 10.57 Theoretical for $C_{14}H_{14}N_2O_3$: C 65.1; H 5.46; N 10.85; T.L.C. = eluent: AcOEt:EtOH = 170:30 $R_f$ ≃ 0.37; N.M.R. ($CDCl_3$) δ p.p.m.: 1.34 (3H, d, $$-CH-CH_3)$$
$$\phantom{-}|$$

3.86 (3H, s, —O—CH$_3$) 4.52–4.70 (2H, m, $$-O-CH-CH-)$$
$$\phantom{-O-}|\phantom{CH-}|$$

6.46–7.83 (6H, m, aromatics + imidazole);
trans-2-methyl-3-(1-imidazolyl)-2,3-dihydro-5-hydroxy-4H-1-benzopyran-4-one; m.p. = 132°–137° C.;

Analysis of the elements: Found: C 62.98; H 4.97; N 11.22 Theoretical for $C_{13}H_{12}N_2O_3$: C 63.92; H 4.95; N 11.46; T.L.C. = eluent: AcOEt:EtOH = 170:30 $R_f \approx 0.4$;

trans-2-methyl-3-(1-imidazolyl)-2,3-dihydro-7-hydroxy-4H-1-benzopyran-4-one; m.p. = 250°-251° C.;

Analysis of the elements: Found: C 63.13; H 4.82; N 11.26 Theoretical for $C_{13}H_{12}N_2O_3$: C 63.92; H 4.95; N 11.46; T.L.C. = eluent: AcOEt:EtOH = 170:30 $R_f \approx 0.35$; N.M.R. ($CF_3COOD$-$CDCl_3$) δ p.p.m.: 1.53 (3H, d, —C$\underline{H}_3$) 5.00 (1H, m,

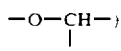

5.44 (1H, d,

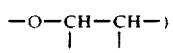

6.89-8.89 (6H, m, aromatics + imidazole;

trans-2-methyl-3-(1-imidazolyl)-2,3-dihydro-6-tert-butyl-7-hydroxy-4H-1-benzopyran-4-one; m.p. = 266°-268° C.;

Analysis of the elements: Found: C 67.53; H 6.75; N 9.24 Theoretical for $C_{17}H_{20}N_2O_3$: C 67.98; H 6.71; N 9.33; T.L.C. = eluent: AcOEt:EtOH:NH$_4$OH 32% = 85:15:1 $R_f \approx 0.5$; N.M.R. (DMSO-d$_6$; CDCl$_3$) δ p.p.m.: 1.21 (3H, d,

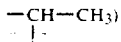

1.35 (9H, s, tert.butyl) 4.83 (1H, dq,

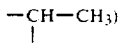

5.20 (1H, d,

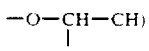

6.43-7.63 (5H, m, aromatics + imidazole) 10 (1H, broad s, O—$\underline{H}$);

trans-2-methyl-3-(1-imidazolyl)-2,3-dihydro-5-hydroxy-6,8-di tert.butyl-4H-1-benzopyran-4-one; m.p. = 166°-171° C.;

Analysis of the elements: Found: C 70.40; H 7.94; N 7.75 Theoretical for $C_{21}H_{28}N_2O_3$: C 70.76; H 7.91; N 7.86; T.L.C. = eluent: AcOEt:EtOH:NH$_4$OH 32% = 85:15:1 $R_f \approx 0.5$; N.M.R. (CDCl$_3$) δ p.p.m.: 1.38 (9H, s, tert.butyl) 1.39 (9H, s, tert.butyl) 1.40 (3H, d,

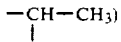

4.67 (1H, dq,

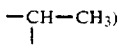

4.90 (1H, d,

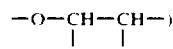

6.89-7.58 (4H, m, aromatics + imidazole) 12.8 (1H, s, —O—$\underline{H}$);

trans-2-methyl-3-(1-imidazolyl)-2,3-dihydro-6-carboxy-4H-1-benzopyran-4-one; m.p. = >250° C.;

Analysis of the elements: Found: C 60.85; H 4.45; N 10.8 Theoretical for $C_{14}H_{12}N_2O_2$: C 61.76; H 4.44; N 10.28; N.M.R. (DMSO-d$_6$) δ p.p.m.: 1.22 (3H, d,

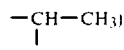

5.25 (1H, m,

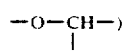

5.72 (1H, d,

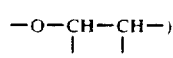

7.03-8.36 (6H, m, aromatics + imidazole);

trans-2-methyl-3-(1-imidazolyl)-2,3-dihydro-6-carboxy-8-bromo-4H-1-benzopyran-4-one; m.p. = 276°-281° C.;

Analysis of the elements: Found: C 47.02; H 3.14; N 7.68; Br 22.05 Theoretical for $C_{14}H_{11}BrN_2O_4$: C 47.88; H 3.15; N 7.97; Br 22.75; N.M.R. (DMSO-d$_6$) δ p.p.m.: 1.25 (3H, d, —C$\underline{H}_3$) 5.30 (1H, m,

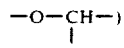

5.70 (1H, d,

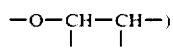

7.00-8.37 (5H, m, aromatics + imidazole);

trans-2-methyl-3-(1-imidazolyl)-2,3-dihydro-6-ethoxycarbonyl-8-bromo-4H-1-benzopyran-4-one; m.p. = 65°-70° C.;

Analysis of the elements: Found: C 50.43; H 4.07; N 7.1; Br 20.08 Theoretical for $C_{16}H_{15}BrN_2O_4$: C 50.67; H 3.98; N 7.38; Br 21.07; N.M.R. (CDCl$_3$) δ p.p.m.: 1.38 (3H, t, —CH$_2$—C$\underline{H}_3$) 1.44 (3H, d, —CH—C$\underline{H}_3$) 4.36 (2H, q, —C$\underline{H}_2$—C$\overline{H}_3$) 4.90 (2H, m,

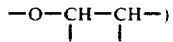

6.84-8.48 (5H, m, aromatics + imidazole);

2-methyl-3-(1-imidazolyl)-2,3-dihydro-6-bromo-7-methoxy-4H-1-benzopyran-4-one; m.p. = 80°-90° C. (dec.);

Analysis of the elements: Found: C 49.0; H 3.65; N 8.2; Br 23.1 Theoretical for $C_{14}H_{13}BrN_2O_3$: C 49.88; H 3.85; N 8.3; Br 23.7; N.M.R. (DMSO-d6) δ p.p.m.: 1.19 (3H, d,

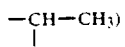

3.96 (3H, s, —O—CH3) 5.14 (1H, m,

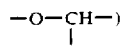

5.50 (1H, d,

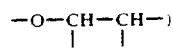

6.86–7.88 (5H, m, aromatics+imidazole);

trans-2-methyl-3-(1-imidazolyl)-2,3-dihydro-6-n.propyl-7-hydroxy-4H-1-benzopyran-4-one;

m.p.=120°–125° C. (dec.);

Analysis of the elements: Found: C 67.02; H 6.29; N 9.68 Theoretical for: $C_{16}H_{18}N_2O_3$: C 67.11; H 6.33; N 9.78; T.L.C.=eluent: $CHCl_3:CH_3CH_2OH=90:10$ $R_f=0.3$;

trans-2-methyl-3-(1-imidazolyl)-2,3-dihydro-6-n.propyl-7-methoxy-4H-1-benzopyran-4-one;

Analysis of the elements: Found: C 67.81; H 6.68; N 9.29 Theoretical for: $C_{17}H_{20}N_2O_3$: C 67.98; H 6.71; N 9.33 T.L.C.=eluent: $CHCl_3:CH_3CH_2OH=90:10$ $R_f=0.6$;

2-methyl-3-(1-imidazolyl)-2,3-dihydro-6-methoxy-4H-1-benzopyran-4-one;

2-methyl-3-(1-imidazolyl)-2,3-dihydro-6-hydroxy-4H-1-benzopyran-4-one;

2-methyl-3-(1-imidazolyl)-2,3-dihydro-6-(4-hydroxy)-phenyl-4H-1-benzopyran-4-one;

2-[(3,4-dihydroxy)-phenyl]-3-(1-imidazolyl)-2,3-dihydro-5,7-dihydroxy-4H-1-benzopyran-4-one; and 2-n.propyl-3-(1-imidazolyl)-2,3-dihydro-6-carboxy-4H-1-benzopyran-4-one.

EXAMPLE 2

A mixture of 2-hydroxy-α-(1-imidazolyl)-acetophenone (3.5 g), and benzaldehyde (200 ml) was heated at 110° C. for 8 hours.

The benzaldehyde was evaporated under reduced pressure and the residue, taken up with $CH_2Cl_2$ (100 ml), washed with $H_2O$, was extracted with a solution of 8% HCl.

The acid solution, neutralized with $NaHCO_3$, extracted with $CH_2Cl_2$, dried and evaporated, gave 2 g of trans 2-phenyl-3-(1-imidazolyl)-2,3-dihydro-4H-1-benzopyran-4-one m.p. 199°–203° C.

Analysis of the elements: Found: C 73.81; H 4.79; N 9.47 Theoretical for $C_{18}H_{14}N_2O_2$: C 74.47; H 4.86; N 9.64; T.L.C.: eluent: $CH_2Cl_2:MeOH=180:20$ $R_f=0.45$; N.M.R.=($CDCl_3$) p.p.m. 5.19 (1H d

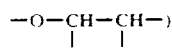

5.48 (1H d

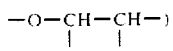

7.75–8.10 (12H m aromatics+imidazole) J

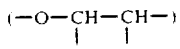

≃12 Hz.

Analogously, the following compounds were prepared:

trans-2-(3-pyridyl)-3-(1-imidazolyl)-2,3-dihydro-4H-1-benzopyran-4 one; m.p. 70° C. (dec.);

Analysis of the elements: Found: C 69.95; H 4.55; N 13.98 Theoretical for $C_{17}H_{13}N_3O_2$: C 70.09; H 4.49; N 14.42; T.L.C.: eluent: $AcOEt:MeOH:CH_3COOH=180:20:6$ $R_f=0.35$; N.M.R. ($CDCl_3$) δ p.p.m.: 5.20 (1H d

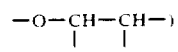

5.60 (1H d

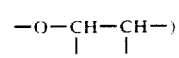

8.00 (1H d of d

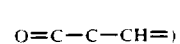

8.58 (2H m

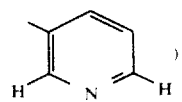

J

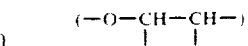

≃12 Hz;

2-phenyl-3-(1-imidazolyl)-2,3-dihydro-6-carboxy-4H-1-benzopyran-4-one; and 2-(4-pyridyl)-3-(1-imidazolyl)-2,3-dihydro-7-hydroxy-4H-1-benzopyran-4-one.

EXAMPLE 3

A mixture of 2-hydroxy-α-(1-imidazolyl)-acetophenone (1 g) and 10 ml of n-butyl glyoxylate was stirred at room temperature for 1 hour.

The mixture, taken up with ethyl acetate, was extracted with a solution of 8% HCl.

The acid solution, neutralized with $NaHCO_3$, extracted with ethyl ether, dried and evaporated, gave 0.8 g of 2-n.butoxycarbonyl-3-(1-imidazolyl)-2,3-dihydro-4H-1-benzopyran-4 one;

Analysis of the elements: Found: C 64.25; H 5.70; N 8.88 Theoretical for: $C_{17}H_{18}N_2O_4$: C 64.95; H 5.77; N 8.91; N.M.R. (CDCl$_3$) δ p.p.m.: 0.86 (3H t —C$\underline{H}_3$) 1.0–1.7 (4H m —C$\underline{H}_2$—C$\underline{H}_2$—CH$_3$) 4.06 (2H t —O—C$\underline{H}_2$—) 4.86 (1H d

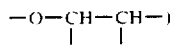

6.19 (1H d

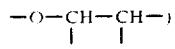

6.7–7.72 (7H m aromatics and imidazole)

Analogously, the following compounds were prepared:

2-methoxycarbonyl-3-(1-imidazolyl)-2,3-dihydro-4H-1-benzopyran-4-one; and 2-carboxy-3-(1-imidazolyl)-2,3-dihydro-4H-1-benzopyran-4-one.

EXAMPLE 4

A mixture of 2,2-dimethyl-3-bromo-2,3-dihydro-6-tert.butyl-7-hydroxy-4H-1-benzopyran-4-one (1.5 g) and imidazole (15 g) was heated at 100° C. for 12 hours.

The mixture taken up with CH$_2$Cl$_2$ (200 ml), washed with H$_2$O, was extracted with a solution of 8% HCl.

The acid solution, neutralized with NaHCO$_3$, extracted with CH$_2$Cl$_2$, dried and evaporated, gave 0.8 g of 2,2-dimethyl-3-(1-imidazolyl)-2,3-dihydro-6-tert. butyl-7-hydroxy-4H-1-benzopyran-4 one;

Elemental analysis Found: C 67.9; H 7.0; N 8.57 Calculated for $C_{18}H_{22}N_2O_2$: C 68.76; H 7.05; N 8.91; T.L.C. = eluent CH$_2$Cl$_2$:CH$_3$OH = 180:20 R$_f$=0.45; N.M.R. (CDCl$_3$) δ p.p.m.: 1.03 (3H s —C$\underline{H}_3$) 1.39 (9H s tert butyl) 1.50 (3H s —C$\underline{H}_3$) 5.23 (1H s

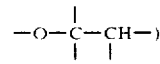

6.40 (1H s

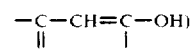

6.71 (1H s large

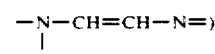

7.06 (2H s large

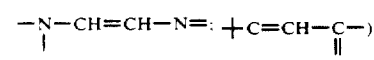

7.43 (1H s large

—N—C$\underline{H}$=N—).

Analogously, the following compound was prepared: 2,2-dimethyl-3-(1-imidazolyl)-2,3-dihydro-4H-1-benzopyran-4-one.

EXAMPLE 5

NaBH$_4$ (0.6 g) was added portionwise to a solution of 2-methyl-3-(1-imidazolyl)-2,3-dihydro-4H-1-benzopyran-4 one (1.3 g) in MeOH (70 ml) at room temperature. The mixture, stirred for 2 hours, added with water (300 ml), extracted with CHCl$_3$, dried and evaporated to dryness gave 2-methyl-3-(1-imidazolyl)-2.3-dihydro-4H-1-benzopyran-4-ol (1.3 g); m.p. = 160°–175° C.;

Analysis of the elements: Found: C 67.56; H 6.22; 11.93 Theoretical for $C_{13}H_{14}N_2O_2$: C 67.81; H 6.12; N 12.16; I.R. (KBr) cm$^{-1}$ Stretching (OH) 3200–2300 Stretching (C—H) aromatics 3060, 3030 Stretching (C—H) alifactis 2980, 2930, 2880 Stretching (C=C,C=N) aromatics 1610, 1580, 1500 Stretching (C—O—C) 1240, 1080.

Analogously, the following compounds were prepared:

2-methyl-3-(1-imidazolyl)-2,3-dihydro-6-carboxy-4H-1-benzopyran-4-ol; m.p. = 100°–105° C.;

Analysis of the elements: Found: C 60.70; H 5.04; N 10.10 Theoretical for $C_{14}H_{14}N_2O_4$: C 61.30; H 5.14; N 10.21; N.M.R. (DMSO-d$_6$) δ p.p.m.: 1.05 (3H, d, —C$\underline{H}_3$) 4.16 (1H, dd,

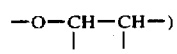

4.65 (1H, m,

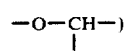

5.14 (1H, d,

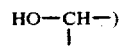

6.90–8.12 (6H, m, aromatics+imidazole); I.R. (KBr) cm$^{-1}$ Stretching

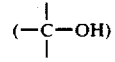

3500–3200 Stretching (OH) carboxylic acid 3000–2200 Stretching (C=O) carboxylic acid 1680.

Analogously, the following compounds were prepared:

2-methyl-3-(1-imidazolyl)-2,3-dihydro-6,8-dibromo-7-hydroxy-4H-1-benzopyran-4-ol;

2-methyl-3-(1-imidazolyl)-2,3-dihydro-6-tert.butyl-7-hydroxy-4H-1-benzopyran-4-ol;

2-methyl-3-(1-imidazolyl)-2,3-dihydro-6-bromo-7-hydroxy-4H-1-benzopyran-4-ol;

2-phenyl-3-(1-imidazolyl)-2,3-dihydro-6-carboxy-4H-1-benzopyran-4-ol; and

2-[(3,4-dihydroxy)-phenyl]-3-(1-imidazolyl)-2,3-dihydro-5,7-dihydroxy-4H-1-benzopyran-4-ol.

EXAMPLE 6

Br$_2$ (0.34 ml) was added dropwise to a solution of trans-2-methyl-3-(1-imidazolyl)-2,3-dihydro-4H-1-benzopyran-4-one (1.5 g) and AlCl$_3$ (2.6 g) in 40 ml of CH$_2$Cl$_2$. The solution was stirred at room temperature for 10 h.

Then water was added giving after acidification with HCl and filtration trans 2-methyl-3-(1-imidazolyl)-2,3-dihydro-6-bromo-4H-1-benzopyran-4-one hydrochloride (2 g); m.p. 250° C. (dec);

Analysis of the elements: Found: C 44.8; H 3.57; N 7.93; Br 24.0; Cl$^-$ 10.35 Theoretical for C$_{13}$H$_{11}$BrN$_2$O$_2$.HCl = C 45.44; H 3.52 N 8.15; Br 23.25; Cl$^-$ 10.31; T.L.C. eluent: CH$_2$Cl$_2$:MeOH = 180:20 R$_f$=0.4; N.M.R. (CF$_3$COOD) δ p.p.m.: 1.56 (3H d —CH$_3$) 5.12 (1H m

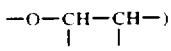

5.64 (1H d

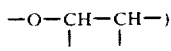

7.13 (1H d

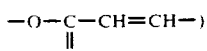

7.6; 7.74 (2H 2 broad s —N—CH=CH—N=) 7.84 (1H dd

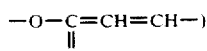

8.10 (1H d

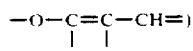

9.09 (1H broad s —N—CH=N—) J

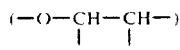

≃12 Hz.

By proceeding analogously the following compounds was obtained:

trans-2-methyl-3-(1-imidazolyl)-2,3-dihydro-6-bromo-7-hydroxy-4H-1-benzopyran-4-one hydrochloride; m.p. = 305°–308° C. (dec.);

Analysis of the elements: Found: C 43.84; H 3.30; N 7.76; Br 21.22; Cl$^-$ 10.10 Theoretical for C$_{13}$H$_{11}$BrN$_2$O$_3$.HCl: C 43.42; H 3.36; N 7.79; Br 22.22; Cl 9.86; T.L.C. = eluent: CH$_2$Cl$_2$:CH$_3$OH = 180:20 R$_f$=0.35; N.M.R. (DMSO-d$_6$) δ p.p.m.: 1.30 (3H, d,

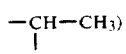

5.20 (1H, m,

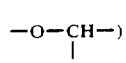

5.97 (1H, d,

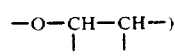

6.84–9.31 (5H, m, aromatics + imidazole).

EXAMPLE 7

A solution of CH$_3$I (0.66 g) in anhydrous tetrahydrofurane (15 ml) was added to metallic anhydrous magnesium. A small crystal of iodine was added to the mixture, which was stirred at room temperature for one hour and then cooled in a cold water bath.

A solution of 2-methyl-3-(1-imidazolyl)-2,3-dihydro-4H-1-benzopyran-4-one (0.53 g) in anhydrous tetrahydrofurane (20 ml) was added to the reaction mixture, which was refluxed moderately for 30 minutes and then for 1 hour on a water bath. The mixture was cooled, poured into a mixture of crushed ice and water (100 ml) and extracted with CHCl$_3$ (100 ml). The organic layer, dried on anhydrous Na$_2$SO$_4$ and evaporated to dryness under vacuum, afforded 2-methyl-3-(1-imidazolyl)-2,3-dihydro-4-methyl-benzopyran-4-ol (0.3 g);

Analysis of the elements: Found: C 66.95; H 6.29; N 11.01 Theoretical for C$_{14}$H$_{16}$N$_2$O$_2$ = C 68.83; H 6.59; N 11.46; I.R. (KBr) cm$^{-1}$ Stretching (OH)3200–2300 (C=C,C=N) aromatics 1610–1580–1500

EXAMPLE 8

2-Methyl-3-(1-imidazolyl)-2,3-dihydro-6-bromo-4H-1-benzopyran-4-one was treated with a stoichiometric amount of hydrogen chloride, to give 2-methyl-3-(1-imidazolyl)-2,3-dihydro-6-bromo-4H-1-benzopyran-4-one hydrochloride. m.p. 250° C. (dec.).

EXAMPLE 9

A solution of 2-bromo-7-methoxy-3,4-dihydro-1(2H)-naphthalenone (17.25 g), imidazole (23 g), and N,N-dimethylformamide (110 ml), was stirred for 6 hours at room temperature.

The solution was poured into ice-water and then extracted with CH$_2$Cl$_2$ (3 × 100 ml). The organic phase, after washing with H$_2$O, was extracted with a solution of 8% HCl.

The acid solution was neutralized with NaHCO$_3$, the precipitate was filtered off, washed with H$_2$O and dried 11.5 g of 2-(1-imidazolyl)-3,4-dihydro-7-methoxy-1(2H)-naphthalenone were obtained; m.p. = 113°–115° C.;

Elemental analysis: Found: C 69.44; H 5.82; N 11.59 Calculated for C$_{14}$H$_{14}$N$_2$O$_2$: C 69.40; H 5.82; N 11.56; T.L.C. = eluent CHCl$_3$:CH$_3$OH = 180:20 R$_f$=0.55; N.M.R. Spectrum (CDCl$_3$) δ p.p.m.: 2.42–2.72 (2H, m, CH$_2$ at 3-position) 3.02–3.35 (2H, m, CH$_2$ at 4-position) 3.84 (3H, s, OCH$_3$) 4.96 (1H, dd, CH at 2-position) 6.96–7.58 (6H, m, aromatics + imidazole); I.R. Spectrum (KBr) $\nu_{max}$ cm$^{-1}$: 3040-3020 (aromatics) 2830 (C—O—C) 1700 (C=O).

Analogously, the following compounds were prepared:

2-(1-imidazolyl)-3,4-dihydro-6-methoxy-1(2H)-naphthalenone; m.p.=174°-176° C.;

Elemental Analysis: Found: C 69.08; H 5.86; N 11.41 Calculated for $C_{14}H_{14}N_2O_2$: C 69.40; H 5.82; N 11.56; T.L.C.=eluent CHCl$_3$:CH$_3$OH=180:20 R$_f$=0.62; N.M.R. Spectrum (CDCl$_3$-DMSO-CF$_3$COOD) δ p.p.m.: 2.65 (2H, m, CH$_2$ at 3-position) 3.25 (2H, m, CH$_2$ at 4-position) 3.91 (3H, s, OCH$_3$) 5.66 (1H, dd, CH at 2-position) 6.89-9.18 (6H, m, aromatics+imidazole); I.R. Spectrum (KBr) $\nu_{max}$ cm$^{-1}$: 1680 (C=O) 1250 (C—O—C ether);

2-(1-imidazolyl)-3,4-dihydro-5-methoxy-1(2H)-naphthalenone; m.p.=181°-182° C.;

Elemental analysis: Found: C 69.32; H 5.74; N 11.37 Calculated for $C_{14}H_{14}N_2O_3$: C 69.40; H 5.82; N 11.41; T.L.C.=eluent CHCl$_3$:CH$_3$OH=180:20 R$_f$=0.59; N.M.R. Spectrum (CDCl$_3$) δ p.p.m.: 2.35 (4H, m, CH$_2$ at 3- and 4-positions) 3.91 (3H, s, OCH$_3$) 4.91 (1H, dd, CH at 2-position) 6.91-7.81 (6H, m, aromatics+imidazole); I.R. Spectrum (KBr) $\nu_{max}$ cm$^{-1}$: 1670 (C=O) 1240 (C—O—C ether) 735 (aromatics, bending);

2-(1-imidazolyl)-3,4-dihydro-7-nitro-1(2H)-naphthalenone; m.p.=155° C. (dec.);

Elemental analysis: Found: C 60.70; H 4.26; N 16.11 Calculated for $C_{13}H_{11}N_3O_3$: C 60.69; H 4.31; N 16.33; T.L.C.=eluent CHCl$_3$:CH$_3$OH=180:20 R$_f$=0.43; N.M.R. Spectrum (CDCl$_3$) δ p.p.m.: 2.70 (2H, m, CH$_2$ at 3-position) 3.40 (2H, m, CH$_2$ at 4-position) 5.11 (1H, m, CH at 2-position) 6.98-8.80 (6H, m, aromatics+imidazole); I.R. Spectrum (Nujol) $\nu_{max}$ cm$^{-1}$: 1710 (C=O);

trans-2-(1-imidazolyl)-3-methyl-1-indanone

Elemental analysis Found: C 71.85; H 5.65; N 13.12 Calculated for $C_{13}H_{12}N_2O$: C 73.56; H 5.70; N 13.19; T.L.C.=eluent CHCl$_3$:MeOH=190:10 R$_f$=0.6; N.M.R. Spectrum (CDCl$_3$) δ p.p.m.: 1.81 (3H, d, CH$_3$) 3.50 (1H, m, CH at 3-position) 4.60 (1H, d, CH at 2-position) 6.91-7.62 (7H, m, aromatics+imidazole);

2-(1-imidazolyl)-3,4-dihydro-7-acetylamino-1(2H)-naphthalenone; m.p.=206° C.;

Elemental analysis Found: C 64.68; H 5.48; N 15.10 Calculated for $C_{15}H_{15}N_3O_2$: C 66.90; H 5.61; N 15.60; T.L.C.=eluent CHCl$_3$:CH$_3$OH=180:20 R$_f$=0.29; N.M.R. Spectrum (CDCl$_3$-DMSO) δ p.p.m.: 2.12 (3H, s, CH$_3$CONH) 2.60 (2H, m, CH$_2$ at 3-position) 3.20 (2H, m, CH$_2$ at 4-position) 5.23 (1H, m, CH at 2-position) 7.06-8.10 (6H, m, aromatics+imidazole) 10.02 (1H, br.s., NH amide); I.R. Spectrum (KBr) $\nu_{max}$ cm$^{-1}$: 1680 (C=O) 1610, 1590, 1490 (C=C+C=N);

2-(1-imidazolyl)-3,4-dihydro-6-hydroxy-7-tert.butyl-1(2H)-naphthalenone; m.p. >290° C.;

Elemental analysis Found: C 71.64; H 7.44; N 9.72 Calculated for $C_{17}H_{20}N_2O_2$: C 71.80; H 7.10; N 9.85; T.L.C.=eluent CHCl$_3$:CH$_3$OH=180:20 R$_f$=0.32; N.M.R. Spectrum (DMSO$_{d6}$) δ p.p.m.: 1.37 (9H, s, t-butyl) 2.1-3.2 (4H, m, CH$_2$ at 3- and 4-position) 5.22 (1H, dd, CH at 2-position) 6.74-7.79 (5H, m, aromatics+imidazole);

2-(1-imidazolyl)-3,4-dihydro-7-carboxy-1(2H)-naphthalenone; m.p. >290° C.;

Elemental analysis Found: C 64.71; H 4.56; N 10.48 Calculated for $C_{14}H_{12}N_2O_3$=C 65.61; H 4.72; N 10.93; T.L.C.=eluent: CH$_3$COCH$_3$:H$_2$O:CH$_3$COOH=90:10:5 R$_f$=0.45; N.M.R. Spectrum (CF$_3$COOD) δ p.p.m.: 2.92 (2H, m, CH$_2$ at 3-position) 3.52 (2H, m, CH$_2$ at 4-position) 5.67 (1H, dd, CH at 2-position) 7.57-8.83 (6H, m, aromatics+imidazole); I.R. Spectrum (KBr) δ$_{C=O}$ 1700 cm$^{-1}$;

2-(1-imidazolyl)-3,4-dihydro-5,7-dibromo-6-hydroxy-1(2H)-naphthalenone; m.p. 230°-233° C.;

Elemental analysis Found: C 39.30; H 2.52; N 7.11; Br 41.39 Calculated for $C_{13}H_{10}N_2O_2$Br: C 40.45; H 2.61; N 7.25; Br 41.96; T.L.C.=eluent: CHCl$_3$:CH$_3$OH=170:30 R$_f$=0.29; N.M.R. Spectrum (CF$_3$COOD) δ p.p.m.: 2.90 (2H, m, CH$_2$ at 3-position) 3.1-3.8 (2H, m, CH$_2$ at 4-position) 5.61 (1H, m, CH at 2-position) 7.57-8.83 (4H, m, aromatics+imidazole);

2-(1-imidazolyl)-3,4-dihydro-8-carboxy-1(2H)-naphthalenone; m.p. 280° C.;

Elemental analysis Found: C 65.21; H 4.23; N 10.74 Calculated for $C_{14}H_{12}N_2O_2$: C 65.61; H 4.27; N 10.93; T.L.C.=eluent CH$_3$COCH$_3$:H$_2$O:CH$_3$COOH=20:10:5 R$_f$=0.5; N.M.R. Spectrum (DMSO$_{d6}$) δ p.p.m.: 2.22-2.80 (2H, m, CH$_2$ at 3-position) 3.20 (2H, m, CH$_2$ at 4-position) 5.49 (1H, dd, CH at 2-position) 6.85-7.94 (6H, m, aromatics+imidazole);

2-(1-imidazolyl)-3,4-dihydro-7-methoxy-8-bromo-1(2H)-naphthalenone; m.p. 176°-179° C.;

Elemental analysis Found: C 51.98; H 4.03; N 8.54; Br 24.88 Calculated for $C_{14}H_{13}BrN_2O_2$: C 52.35; H 4.08; N 8.72; Br 24.79; T.L.C.=eluent CHCl$_3$:CH$_3$OH=180:20 R$_f$=0.28; N.M.R. Spectrum (CDCl$_3$-DMSO$_{d6}$) δ p.p.m.: 2.58 (2H, m, CH$_2$ at 3-position) 3.68 (2H, m, CH$_2$ at 4-position) 3.91 (3H, s, OCH$_3$) 5.24 (1H, dd, CH at 2-position) 7.00-7.58 (6H, m, aromatics+imidazole); I.R. Spectrum (KBr) $\nu_{max}$ cm$^{-1}$: 3120-3080-3020 (aromatics) 1715 (C=O) 1590-1550-1500 (C=C+C=N);

2-(1-imidazolyl)-3,4-dihydro-7-phenyl-1(2H)-naphthalenone; m.p. 128°-130° C.;

Elemental analysis Found: C 78.84; H 5.42; N 9.61 Calculated for $C_{19}H_{16}N_2O$: C 79.14; H 5.59; N 9.71; T.L.C.=eluent CHCl$_3$:CH$_3$OH=100:5 R$_f$=0.3; N.M.R. Spectrum (CDCl$_3$) δ p.p.m.: 2.60 (2H, m, CH$_2$ at 3-position) 3.20 (2H, m, CH$_2$ at 4-position) 4.98 (1H, dd, CH at 2-position) 6.92-8.24 (11H, aromatics+imidazole);

2-(1-imidazolyl)-3,4-dihydro-5-allyl-6-hydroxy-1(2H)-naphthalenone; m.p. 225°-230° C.;

Elemental analysis Found: C 70.90; H 5.93; N 10.34 Calculated for $C_{16}H_{16}N_2O_2$: C 71.61; H 6.01; N 10.44; T.L.C.=eluent CHCl$_3$:CH$_3$OH=180:20 R$_f$=0.27; N.M.R. Spectrum (CDCl$_3$-DMSO$_{d6}$) δ p.p.m.: 2.50 (2H, m, CH$_2$ at 3-position) 3.10 (2H, m, CH$_2$ at 4-position) 3.40 (2H, m, CH$_2$ allylic) 4.90 (2H, m, CH$_2$=) 5.18 (1H, m, CH at 2-position) 5.82 (1H, m, =CH—) 6.86-7.73 (5H, m, aromatics+imidazole) 10.38 (1H, br.s., OH); I.R. Spectrum (KBr) $\nu_{max}$ cm$^{-1}$: 3440 (OH) 1675 (C=O) 1630 (C=C) 1590-1570-1500 (C=C+C=N aromatics);

2-(1-imidazolyl)-3,4-dihydro-8-methoxy-1(2H)-naphthalenone;

2-(1-imidazolyl)-3,4-dihydro-5-bromo-7-carboxy-1(2H)-naphthalenone;

2-(1-imidazolyl)-3,4-dihydro-7-hydroxy-8-bromo-1(2H)-naphthalenone;

2-(1-imidazolyl)-3,4-dihydro-3-methyl-1(2H)-naphthalenone;

2-(1-imidazolyl)-3,4-dihydro-3-phenyl-7-carboxy-1(2H)-naphthalenone;

2-(1-imidazolyl)-3,4-dihydro-3-carboxy-1(2H)-naphthalenone;

2-(1-imidazolyl)-5-methoxy-1-indanone; and
2-(1-imidazolyl)-6-carboxy-1-indanone.

EXAMPLE 10

NaBH$_4$ (1 g) was added portionwise to a solution of 2-(1-imidazolyl)-3,4-dihydro-7-methoxy-1(2H)-naphthalenone (1.5 g) in CH$_3$OH (35 ml) at room temperature. The mixture, after stirring at 60° C. for 5 hours, was poured into ice-water. The evaporation of the methanol under reduced pressure gave, after filtering and washing with water, 1.3 g of trans, 2-(1-imidazolyl)-1,2,3,4-tetrahydro-7-methoxy-1-naphthalenol, m.p. = 168°-170° C.;

Elemental analysis Found: C 68.41; H 6.56; N 11.37 Calculated for C$_{14}$H$_{16}$O$_2$N$_2$: C 68.83; H 6.6; N 11.47; T.L.C. = eluent CHCl$_3$:CH$_3$OH = 180:20 R$_f$=0.66; N.M.R. Spectrum (CD$_3$OD) δ p.p.m.: 2.22 (2H, m, CH$_2$ at 3-position) 2.90 (2H, m, CH$_2$ at 4-position) 3.75 (3H, s, OCH$_3$) 4.18 (1H, m, CH at 2-position) 4.75 (1H, d, CH at 1-position) 6.7-7.72 (6H, m, aromatics+imidazole); I.R. Spectrum (KBr) $\nu_{max}$ cm$^{-1}$: 3200-2500 (—OH) 3080-3050 (aromatics) 2835 (C—H methoxy) 870-740 (bending of aromatics).

Analogously, the following compounds were prepared:
2-(1-imidazolyl)-1,2,3,4-tetrahydro-6-hydroxy-7-tert.butyl-1-naphthalenol;
2-(1-imidazolyl)-1,2,3,4-tetrahydro-5-bromo-6-hydroxy-1-naphthalenol;
2-(1-imidazolyl)-1,2,3,4-tetrahydro-7-carboxy-1-naphthalenol; and
2-(1-imidazolyl)-1,2,3,4-tetrahydro-8-carboxy-1-naphthalenol.

EXAMPLE 11

A solution of CH$_3$I (0.78 g) in anhydrous tetrahydrofuran (15 ml) was added dropwise at 20°-30° C. under nitrogen to a suspension of magnesium turnings (0.133 g) in anhydrous tetrahydrofuran (20 ml) containing a catalitic amount of iodine. The mixture was stirred for 1 hour, until the complete disappearance of the magnesium, and then cooled to 0° C. with a ice-water bath.

A solution of 2-(1-imidazolyl)-3,4-dihydro-7-methoxy-1(2H)-naphthalenone (1.2 g) in anhydrous tetrahydrofuran (20 ml) was added at 0°-5° C. to the reaction mixture, which was stirred at room temperature for 1 hour and then moderately refluxed for an other hour.

The mixture was cooled, poured into ice-water (100 ml) and extracted with CHCl$_3$ (100 ml). The organic layer, dried on anhydrous Na$_2$SO$_4$ and evaporated to dryness under vacuum, afforded 0.9 g of 1-methyl-2-(1-imidazolyl)-1,2,3,4-tetrahydro-7-methoxy-1-naphthalenol;

Elemental analysis Found: C 68.91; H 6.87; N 12.32 Calculated for C$_{15}$H$_{18}$O$_2$N$_2$: C 69.74; H 7.02; N 12.38; N.M.R. Spectrum (CDCl$_3$) δ p.p.m.: 1.4 (3H, s, CH$_3$) 2.29 (2H, m, CH$_2$ at 3-position) 2.92 (2H, m, CH$_2$ at 4-position) 3.78 (3H, s, OCH$_3$) 4.31 (1H, m, CH at 2-position) 6.85-7.9 (6H, m, aromatics+imidazole).

EXAMPLE 12

2-(1-imidazolyl)-3,4-dihydro-6-methoxy-1(2H-naphthalenone (1.5 g) was refluxed with 48% hydrobromic acid (40 ml) for 5 hours. The solution was poured into ice-water, the solid was filtered off, washed with water and dried, giving 1.3 g of 2-(1-imidazolyl)-3,4-dihydro-6-hydroxy-1(2H)-naphthalenone hydrobromide; m.p. = 298°-300° C.;

Elemental analysis Found: C 49.98; H 4.15; N 8.87; Br 25.88 Calculated for C$_{13}$H$_{13}$BrN$_2$O$_2$: C 50.50; H 4.24; N 9.06; T.L.C. = eluent CHCl$_3$:CH$_3$OH = 180:20 R$_f$=0.56; N.M.R. Spectrum (D$_2$O-DMSO d$_6$) δ p.p.m.: 2.64 (2H, m, CH$_2$ at 3-position) 3.22 (2H, m, CH$_2$ at 4-position) 5.46 (1H, m, CH at 2-position) 6.82-8.84 (6H, m, aromatics+imidazole); I.R. Spectrum (KBr) $\nu_{max}$ cm$^{-1}$: 3440 (OH phenolic) 3100-2400 (NH$^-$) 1660 (C=O).

Analogously, by treatment with 37% HCl instead of 48% HBr, the following compound was prepared:
2-(1-imidazolyl)-3,4-dihydro-5-bromo-6-hydroxy-1(2H)-naphthalenone hydrochloride; m.p. = >300° C.;

Elemental analysis Found: C 44.07; H 3.59; N 7.71; Cl 10.14; Br 22.47 Calculated for C$_{13}$H$_{12}$BrClN$_2$O$_2$: C 45.43; H 3.52; N 8.15; Cl 10.31; Br 23.25; T.L.C. = eluent CHCl$_3$:CH$_3$OH = 170:30 R$_f$=0.56; N.M.R. Spectrum (CF$_3$COOD) δ p.p.m.: 2.7-3.8 (4H, m, CH$_2$ at 3- and 4-positions) 3.82 (1H, dd, CH at 2-position) 7.17-8.86 (5H, m, aromatics+imidazole); I.R. Spectrum (KBr) $\nu_{max}$ cm$^{-1}$: 3550-3300 (OH phenolic) 3120-3040 (aromatics) 1690 (C=O) 620-650 (C—Br).

Similarly the hydrochloride and the hydrobromide of the following compounds were prepared:
2-(1-imidazolyl)-3,4-dihydro-6-hydroxy-7-tert.butyl-1(2H)-naphthalenone;
2-(1-imidazolyl)-3,4-dihydro-5,7-dibromo-6-hydroxy-1(2H)-naphthalenone;
2-(1-imidazolyl)-3,4-dihydro-7-hydroxy-8-bromo-1(2H)-naphthalenone;
2-(1-imidazolyl)-3,4-dihydro-5-allyl-6-hydroxy-1(2H)-naphthalenone;
2-(1-imidazolyl)-1,2,3,4-tetrahydro-6-hydroxy-7-tert.butyl-1-naphthalenol;
2-(1-imidazolyl)-1,2,3,4-tetrahydro-5-bromo-6-hydroxy-1-naphthalenol.

EXAMPLE 13

Br$_2$ (1.28 g) was added dropwise to a solution of 2-(1-imidazolyl)-3,4-dihydro-6-methoxy-1(2H)-naphthalenone (2 g) and AlCl$_3$ (3.2 g) in 40 ml of CH$_2$Cl$_2$. The solution was stirred at room temperature for 5 hours, water (100 ml) was added and the pH adjusted to neutrality with NaHCO$_3$. Extraction with CHCl$_3$ (100 ml), washing with water and drying on anhydrous Na$_2$SO$_4$ gave, after evaporation to dryness under vacuum, 1.5 g of 2-(1-imidazolyl)-3,4-dihydro-5-bromo-6-methoxy-1(2H)-naphthalenone, m.p. = 175°-178° C.;

Elemental analysis Found: C 51.35; H 4.28; N 8.19; Br 24.45 Calculated for C$_{14}$H$_{13}$BrN$_2$O$_2$: C 52.35; H 4.08; N 8.72; Br 24.88; T.L.C. = eluent CHCl$_3$:CH$_3$OH = 170:30 R$_f$=0.73; N.M.R. Spectrum (CDCl$_3$) δ p.p.m.: 2.4-3.7 (4H, m, CH$_2$ at 3- and 4-positions) 4.00 (3H, s, OCH$_3$) 4.93 (1H, dd, CH at 2-position) 6.93-8.08 (5H, m, aromatics+imidazole); I.R. Spectrum (KBr) $\nu_{max}$ cm$^{-1}$ 3140-3100 (aromatics) 1660 (C=O) 1580 (C=N+C=C) 660 (C—Br).

Analogously, the following compounds were prepared:
2-(1-imidazolyl)-3,4-dihydro-5-bromo-6-hydroxy-1(2H)-naphthalenone;
2-(1-imidazolyl)-3,4-dihydro-5,7-dibromo-6-hydroxy-1(2H)-naphthalenone; and
2-(1-imidazolyl)-1,2,3,4-tetrahydro-5-bromo-6-hydroxy-1-naphthalenol.

EXAMPLE 14

A solution of 2-(1-imidazolyl)-3,4-dihydro-7-acetyl-amino-1(2H)-naphthalenone (1.8 g) in ethanol (35 ml) was refluxed with 37% hydrochloric acid (10 ml) for 3 hours. The mixture was cooled, the solid was filtered off, washed with cold ethanol and then dissolved in water (200 ml). The solution was neutralized with 2N NaOH, the solid was filtered off and washed with water, giving, after drying, 1.5 g of 2-(1-imidazolyl)-3,4-dihydro-7-amino-1(2H)-naphthalenone; m.p. = 212°–213° C.;

Elemental analysis Found: C 68.19; H 5.77; N 18.38 Calculated for $C_{13}H_{13}N_3O$: C 68.70; H 5.76; N 18.49; T.L.C. = eluent $CDCl_3:CH_3OH = 180:20$ $R_f = 0.4$; N.M.R. Spectrum (DMSO $d_6$) δ p.p.m.: 2.3–2.8 (2H, m, $CH_2$ at 3-position) 2.84–5.22 (2H, m, $CH_2$ at 4-position) 5.16 (2H, bs, $NH_2$) 5.57 (1H, dd, CH at 2-position) 6.91–8.47 (6H, m, aromatics + imidazole); I.R. Spectrum (Nujol) $\nu_{max}$ cm$^{-1}$: 1680 (C=O).

EXAMPLE 15

A solution of 2-(1-imidazolyl)-3,4-dihydro-7-amino-1(2H)-naphthalenone (1.3 g), $CH_3I$ (3 ml) and $(C_2H_5)_3N$, (1.7 ml) in ethanol (100 ml) was refluxed for 20 hours. The solvent was evaporated under reduced pressure and the residue was taken up with water (100 ml). The solution was neutralized with 2N NaOH and extracted with ethyl acetate (100 ml). The organic layer, dried on anhydrous $Na_2SO_4$ and evaporated under vacuum, gave 1.15 g of 2-(1-imidazolyl)-3,4-dihydro-7-dimethylamino-1(2H)-naphthalenone;

m.p. = 160°–162° C.; Elemental analysis Found: C 68.10; H 5.70; N 18.36 Calculated for $C_{13}H_{13}N_3O$: C 68.70; H 5.76; N 18.49; T.L.C. = eluent $CHCl_3:CH_3OH = 190:10$ $R_f = 0.35$; N.M.R. ($CDCl_3$) δ p.p.m. 2.57 (2H, m, $CH_2$ at 3-position) 2.98 (6H, s, $N(CH_3)_2$) 3.11 (2H, m, $CH_2$ at 4-position) 4.94 (1H, dd, CH at 2-position) 6.95–7.60 (6H, m, aromatics + imidazole).

EXAMPLE 16

A solution of α-(1-imidazolyl)-α-ethyliden-2-bromomethyl-acetophenone (1.53 g) in anhydrous tetrahydrofuran (30 ml) was added dropwise under nitrogen to a suspension of magnesium turnings (0.133 g) in anhydrous tetrahydrofuran (30 ml) containing a small crystal of iodine.

The addition was effected at such a rate that a gentle reflux was maintained.

The mixture was then refluxed for one hour, cooled and poured into ice-water. After acidification to pH5 with $H_2SO_4$ the solution was extracted with ethyl acetate (200 ml). The organic layer, dried and evaporated under vacuum, gave 1.05 g of trans, 2-(1-imidazolyl)-3,4-dihydro-3-methyl-1(2H)-naphthalenone; m.p. = 153°–155° C.;

Elemental analysis Found: C 74.13; H 6.17; N 12.21 Calculated for $C_{14}H_{14}N_2O$: C 74.31; H 6.24; N 12.38; T.L.C. = eluent $CHCl_3:CH_3OH = 180:20$ $R_f = 0.56$; N.M.R. Spectrum ($CDCl_3$) δ p.p.m.: 0.99 (3H, d, $CH_3$) 2.70 (1H, m, CH at 3-position) 2.99–3.25 (2H, m; $CH_2$ at 4-position) 4.58 (1H, d, CH at 2-position) 6.87–8.04 (7H, m, aromatics + imidazole); I.R. Spectrum (KBr) $\nu_{max}$ cm$^{-1}$: 1690 (C=O) 760 (aromatics 1,2 substituted).

By proceeding analogously, the following compounds were prepared:

2-(1-imidazolyl)-3,4-dihydro-8-carboxy-1(2H)-naphthalenone;

2-(1-imidazolyl)-3,4-dihydro-7-carboxy-1(2H)-naphthalenone;

2-(1-imidazolyl)-3,4-dihydro-3-phenyl-7-carboxy-1(2H)-naphthalenone; and 2-(1-imidazolyl)-3,4-dihydro-3-carboxy-1(2H)-naphthalenone.

EXAMPLE 17

A solution of 2,5,7-tribromo-3,4-dihydro-1(2H)-naphthalenone (1 g), imidazole (0.7 g), and N,N-dimethylformamide (15 ml) was stirred at room temperature for 5 hours.

The solvent was evaporated under reduced pressure and the residue, taken up with $CH_2Cl_2$ (20 ml), washed with $H_2O$, was extracted with a solution of 8% HCl.

The acid solution, neutralized with $NaHCO_3$, extracted with $CH_2Cl_2$, dried and evaporated, gave 0.6 g of 2-(1-imidazolyl)-3,4-dihydro-5,7-dibromo-1(2H)-naphthalenone; m.p. = 180°–184° C.;

Elements analysis Found: C 43.19; H 2.6; N 7.26; Br 44.98 Calculated for $C_{13}H_{10}Br_2N_2O$: C 42.19; H 2.72; N 7.57; Br 43.18; T.L.C. = eluent $CH_2Cl_2:CH_3OH = 175:32$ $R_f = 0.5$; N.M.R. Spectrum ($CH_3COOD/CDCl_3$) δ p.p.m.: 2.7–3.1 (2H, m, $CH_2$ at 3-position) 3.1–3.8 (2H, $CH_2$ at 4-position) 5.51 (1H, m, CH at 2-position) 7.77–8.80 (6H, m, aromatics + imidazole).

By proceeding analogously 2-(1-imidazolyl)-3,4-dihydro-1(2H)-naphthalenone was prepared, that, treated with a stoichiometric amount of nitric acid, gave 2-(1-imidazolyl)-3,4-dihydro-1(2H)-naphthalenone nitrate; m.p. = 165°–170° C. (dec.);

Elemental analysis Found: C 56.36; H 4.62; N 15.00 Calculated for $C_{13}H_{12}N_2O \cdot HNO_3$: C 56.72; H 4.76; N 15.26; T.L.C. = eluent $CHCl_3:CH_3OH:NH_4OH$ 35% = 170:30:2 $R_f = 0.5$.

EXAMPLE 18

2-(1-imidazolyl)-3,4-dihydro-6-hydroxy-1(2H)-naphthalenone hydrobromide (1.35 g) was dissolved in water. The solution, basified with $NaHCO_3$, extracted with $CH_2Cl_2$, dried and evaporated, gave 1.15 g of 2-(1-imidazolyl)-3,4-dihydro-6-hydroxy-1(2N)-naphthalenone.

By proceeding analogously all the compounds reported in Example 12 were obtained as free bases, in particular, for example, 2-(1-imidazolyl)-3,4-dihydro-5-bromo-6-hydroxy-1(2H)-naphthalenone.

FORMULATION EXAMPLES

Formulation I: Tablet

Tablets, each weighing 300 mg and containing 100 mg of the active substance are manufactured as follows:

| Composition (for 10,000 tablets) | |
|---|---|
| 2-(1-imidazolyl)-3,4-dihydro-5-bromo-6-hydroxy-1(2H)-naphthalenone | 1000 g |
| Lactose | 1420 g |
| Corn starch | 475 g |
| Talc powder | 75 g |
| Magnesium stearate | 30 g |

2-(1-imidazolyl)-3,4-dihydro-5-bromo-6-hydroxy-1(2H)-naphthalenone, lactose, and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the quantity of starch, talc and magnesium stearate is added, carefully mixed, and processed into tablets using punches of 10 mm diameter.

Formulation II: intramuscular injection

An injectable pharmaceutical composition was manufactured by dissolving 50–100 mg of 2-(1-imidazolyl)-3,4-dihydro-5-bromo-6-hydroxy-1(2H)-naphthalenone hydrochloride in sterile aqueous normal saline solution (1–2 ml).

Formulation III: Capsule

By usual pharmaceutical methods, capsules having the following composition were prepared:

| | |
|---|---|
| 2-(1-imidazolyl)-3,4-dihydro-5-bromo-6-hydroxy-1(2H)-naphthalenone | 50 mg |
| Lactose | 298 mg |
| Corn starch | 50 mg |
| Magnesium stearate | 2 mg |

Formulation IV: Suppository

By usual pharmaceutical methods, suppositories having the following composition were prepared:

| | |
|---|---|
| 2-(1-imidazolyl)-3,4-dihydro-5-bromo-6-hydroxy-1(2H)--naphthalenone | 0.05 g |
| Lecithin | 0.07 g |
| Cocoa butter | 0.88 g |

Formulation V: Tablet

By proceeding analogously to Formulation I, tablets each weighing 300 mg and containing 100 mg of the active substance are manufactured as follows:

| Composition (for 10.000 tablets) | |
|---|---|
| trans-2-(1-imidazolyl)-3-methyl-1-indanone | 1000 g |
| Lactose | 1420 g |
| Corn starch | 475 g |
| Talc powder | 75 g |
| Magnesium stearate | 30 g |

Formulation VI: Capsule

By usual pharmaceutical methods, capsules having the following composition were prepared:

| | |
|---|---|
| trans-2-(1-imidazolyl)-3-methyl-1-indanone | 50 mg |
| Lactose | 298 mg |
| Corn starch | 50 mg |
| Magnesium stearate | 2 mg |

Formulation VII: Suppository

By usual pharmaceutical methods, suppositories having the following composition were prepared:

| | |
|---|---|
| trans-2-(1-imidazolyl)-3-methyl-1-indanone | 0.05 g |
| Lecithin | 0.07 g |
| Cocoa butter | 0.88 g |

Formulation VIII: Tablet

By proceeding analogously to Formulation I, tablets each weighing 300 mg and containing 100 mg of the active substance are manufactured as follows:

| Composition (for 10.000 tablets) | |
|---|---|
| 2-(1-imidazolyl)-3,4-dihydro-5,7-dibromo-1(2H)-naphthalenone | 1000 g |
| Lactose | 1420 g |
| Corn starch | 475 g |
| Talc powder | 75 g |
| Magnesium stearate | 30 g |

Formulation IX: Intramuscular injection

An injectable pharmaceutical composition was manufactured by dissolving 50–100 mg of 2-(1-imidazolyl)-3,4-dihydro-1(2H)-naphthalenone nitrate in sterile water or sterile aqueous normal saline solution (1–2 ml).

Formulation X: Capsule

By usual pharmaceutical methods, capsules having the following composition were prepared:

| | |
|---|---|
| 2-(1-imidazolyl)-3,4-dihydro-5,7-dibromo-1(2H)-naphthalenone | 50 mg |
| Lactose | 298 mg |
| Corn starch | 50 mg |
| Magnesium stearate | 2 mg |

Formulation XI: Suppository

By usual pharmaceutical methods suppositories having the following composition were prepared:

| | |
|---|---|
| 2-(1-imidazolyl)-3,4-dihydro-5,7-dibromo-1(2H)-naphthalenone | 0.05 g |
| Lecithin | 0.07 g |
| Cocoa butter | 0.88 g |

We claim:

1. A pharmaceutical composition having hypolipaemic activity containing a suitable carrier and/or diluent and a therapeutically effective amount of a compound of formula (I)

wherein:

Z completes a bond or is a $$-\underset{\underset{R_6}{\diagdown}}{\overset{\overset{R_5}{\diagup}}{C}}-$$

group, wherein each of $R_5$ and $R_6$, being the same or different, is hydrogen or $C_1$–$C_4$ alkyl;

one of $R_1$ and $R_2$ is hydroxy and the other is hydrogen or $C_1$–$C_6$ alkyl, or $R_1$ and $R_2$, taken together, form an oxo group;

one of $R_3$ and $R_4$ is hydrogen or $C_1$–$C_4$ alkyl and the other represents hydrogen or:

(a) $C_1$–$C_8$ alkyl, unsubstituted or substituted by one or more substituents chosen from halogen; hydroxy, cyano; —COOR′, wherein R′ is hydrogen or $C_1$–$C_6$ alkyl;

$$-N\diagdown_{R''}^{R'} \text{ or } -CON\diagdown_{R''}^{R'},$$

wherein each of R' and R", being the same or different, represents hydrogen or $C_1$-$C_6$ alkyl;
(b) straight or branched $C_1$-$C_4$ alkyl or $C_2$-$C_4$ alkenyl, each substituted by a $C_1$-$C_4$ alkyl, or a $C_3$-$C_7$ monocycloalkyl;
(c) cyano;

$$-COR', -OR', -COOR' \text{ or } -CON\diagdown_{R''}^{R'},$$

wherein R' and R" are as defined above;
each of $X_1$, $X_2$, $X_3$, and $X_4$, which may be the same or different, is hydrogen; halogen; hydroxy; nitro; cyano, $C_1$-$C_6$ alkyl; $C_2$-$C_6$ alkenyl; $C_1$-$C_6$ alkoxy; trihalo-$C_1$-$C_6$ alkyl;

$$-SR', -S-S-R', -COOR', -N\diagdown_{R''}^{R'} \text{ or } -CON\diagdown_{R''}^{R'},$$

R' and R" being as defined above; or a $C_2$-$C_4$ acylamino group; or one of $X_1$, $X_2$, $X_3$ and $X_4$ is phenyl, phenylthio, phenoxy or benzyl, the phenyl, phenylthio, phenoxy or benzyl groups being unsubstituted or substituted by one or more substituents chosen from halogen, $C_1$-$C_6$ alkyl, hydroxy, $C_1$-$C_6$ alkoxy, —SR' or —S—S—R', wherein R' is as defined above, and the others are as defined above; or any two adjacent $X_1$, $X_2$, $X_3$ and $X_4$ groups, taken together, complete a saturated or unsaturated 6-membered carbocyclic ring fused to the benzene ring shown in formula (I), the carbocyclic ring being unsubstituted or substituted by one or more substituents selected from halogen, $C_1$-$C_6$ alkyl, halo-$C_1$-$C_6$ alkyl, $C_1$-$C_6$ alkoxy, —SR' or —S—S—R', wherein R' is as defined above, and any groups $X_1$ to $X_4$ not participating in the completion of such a fused ring are as defined above; provided that:
when Z is a group $$-\underset{R_5}{\overset{-C-}{\diagup}}\underset{R_6}{\diagdown}$$

and, at the same time, at least one of $R_3$ and $R_4$ is different from hydrogen, then $R_5$ and $R_6$ are both hydrogen; and
when Z is a group $$-\underset{R_5}{\overset{-C-}{\diagup}}\underset{R_6}{\diagdown}$$

and, at the same time, at least one of $R_5$ and $R_6$ is different from hydrogen, then $R_3$ and $R_4$ are both hydrogen, or a pharmaceutically acceptable salt thereof.

2. A method of producing a hypolipaemic effect in a patient in need of such effect, said method comprising administering to said patient a therapeutically effective amount of a compound of formula (I)

(I)

wherein:
Z completes a bond or is a $$-\underset{R_5}{\overset{-C-}{\diagup}}\underset{R_6}{\diagdown}$$

group, wherein each of $R_5$ and $R_6$, being the same or different, is hydrogen or $C_1$-$C_4$ alkyl;
one of $R_1$ and $R_2$ is hydroxy and the other is hydrogen or $C_1$-$C_6$ alkyl, or $R_1$ and $R_2$, taken together, form an oxo group;
one of $R_3$ and $R_4$ is hydrogen or $C_1$-$C_4$ alkyl and the other represents hydrogen or:
(a) $C_1$-$C_8$ alkyl, unsubstituted or substituted by one or more substituents chosen from halogen; hydroxy, cyano; —COOR', wherein R' is hydrogen or $C_1$-$C_6$ alkyl;

$$-N\diagdown_{R''}^{R'} \text{ or } -CON\diagdown_{R''}^{R'},$$

wherein each of R' and R", being the same or different, represents hydrogen or $C_1$-$C_6$ alkyl;
(b) straight or branched $C_1$-$C_4$ alkyl or $C_2$-$C_4$ alkenyl, each substituted by a $C_1$-$C_4$ alkyl, or a $C_3$-$C_7$ monocycloalkyl;
(c) cyano;

$$-COR', -OR', -COOR' \text{ or } -CON\diagdown_{R''}^{R'},$$

wherein R' and R" are as defined above;
each of $X_1$, $X_2$, $X_3$, and $X_4$, which may be the same or different, is hydrogen; halogen; hydroxy; nitro; cyano, $C_1$-$C_6$ alkyl; $C_2$-$C_6$ alkenyl; $C_1$-$C_6$ alkoxy; trihalo-$C_1$-$C_6$ alkyl;

$$-SR', -S-S-R', -COOR', -N\diagdown_{R''}^{R'} \text{ or } -CON\diagdown_{R''}^{R'},$$

R' and R" being as defined above; or a $C_2$-$C_4$ acylamino group; or one of $X_1$, $X_2$, $X_3$ and $X_4$ is phenyl, phenylthio, phenoxy or benzyl, the phenyl, phenylthio, phenoxy or benzyl groups being unsubstituted or substituted by one or more substituents chosen from halogen, $C_1$-$C_6$ alkyl, hydroxy, $C_1$-$C_6$ alkoxy, —SR' or —S—S—R', wherein R' is as defined above, and the others are as defined above; or any two adjacent $X_1$, $X_2$, $X_3$ and $X_4$ groups, taken together, complete a saturated or unsaturated 6-membered carbocyclic ring fused to the benzene ring shown in formula (I), the carbocyclic ring being unsubstituted or substituted by one or more substituents selected from halogen, $C_1$-$C_6$ alkyl, halo-$C_1$-$C_6$ alkyl, $C_1$-$C_6$ alkoxy, —SR' or —S—S—R', wherein R' is as defined above, and any groups $X_1$ to $X_4$ not participating in the completion of such a fused ring are as defined above; provided that:

when Z is a group

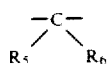

and, at the same time, at least one of $R_3$ and $R_4$ is different from hydrogen, then $R_5$ and $R_6$ are both hydrogen; and when Z is a group

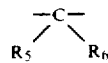

and, at the same time, at least one of $R_5$ and $R_6$ is different from hydrogen, then $R_3$ and $R_4$ are both hydrogen, or a pharmaceutically acceptable salt thereof.

3. A composition according to claim 1, wherein said compound is selected from the group consisting of:
2-(1-imidazolyl)-3,4-dihydro-7-amino-1(2H)-naphthalenone;
2-(1-imidazolyl)-3,4-dihydro-7-dimethylamino-1(2H)-naphthalenone;
2-(1-imidazolyl)-3,4-dihydro-7-acetylamino-1(2H)-naphthalenone;
2-(1-imidazolyl)-3,4-dihydro-7-methoxy-1(2H)-naphthalenone;
2-(1-imidazolyl)-3,4-dihydro-8-methoxy-1(2H)-naphthalenone;
2-(1-imidazolyl)-3,4-dihydro-5-bromo-6-hydroxy-1(2H)-naphthalenone;
2-(1-imidazolyl)-3,4-dihydro-5-bromo-6-methoxy-1(2H)-naphthalenone;
2-(1-imidazolyl)-3,4-dihydro-6-hydroxy-7-tert.butyl-1(2H)-naphthalenone;
2-(1-imidazolyl)-3,4-dihydro-5,7-dibromo-6-hydroxy-1(2H)-naphthalenone;
2-(1-imidazolyl)-3,4-dihydro-7-carboxy-1(2H)-naphthalenone;
2-(1-imidazolyl)-3,4-dihydro-5-bromo-7-carboxy-1(2H)-naphthalenone;
2-(1-imidazolyl)-3,4-dihydro-8-carboxy-1(2H)-naphthalenone;
2-(1-imidazolyl)-3,4-dihydro-7-methoxy-8-bromo-1(2H)-naphthalenone;
2-(1-imidazolyl)-3,4-dihydro-7-hydroxy-8-bromo-1(2H)-naphthalenone;
2-(1-imidazolyl)-3,4-dihydro-5-allyl-6-hydroxy-1(2H)-naphthalenone;
2-(1-imidazolyl)-3,4-dihydro-7-phenyl-1(2H)-naphthalenone;
2-(1-imidazolyl)-3,4-dihydro-3-methyl-1(2H)-naphthalenone;
2-(1-imidazolyl)-3,4-dihydro-3-carboxy-1(2H)-naphthalenone; and the pharmaceutically acceptable salts thereof.

4. A composition according to claim 1, wherein said compound is selected from the group consisting of:
2-(1-imidazolyl)-1,2,3,4-tetrahydro-7-methoxy-1-naphthalenol;
2-(1-imidazolyl)-1,2,3,4-tetrahydro-7-carboxy-1-naphthalenol;
2-(1-imidazolyl)-1,2,3,4-tetrahydro-6-hydroxy-7-tert.butyl-1-naphthalenol;
2-(1-imidazolyl)-1,2,3,4-tetrahydro-5-bromo-6-hydroxy-1-naphthalenol;
2-(1-imidazolyl)-1,2,3,4-tetrahydro-8-carboxy-1-naphthalenol, both in the form of cis or trans isomer and of their mixture, and the pharmaceutically acceptable salts thereof.

5. A composition according to claim 1, wherein said compound is selected from the group consisting of:
2-(1-imidazolyl)-5-methoxy-1-indanone;
2-(1-imidazolyl)-6-carboxy-1-indanone, and the pharmaceutically acceptable salts thereof.

6. A composition according to claim 1, wherein said compound is
2-(1-imidazolyl)-3-methyl-1-indanone both in the form of cis or trans isomer and of their mixture, and the pharmaceutically acceptable salts thereof.

7. A composition according to claim 1, wherein said compound is
2-(1-imidazolyl)-3,4-dihydro-5-bromo-6-hydroxy-1(2H)-naphthalenone, and the pharmaceutically acceptable salts thereof.

8. A method according to claim 2, wherein said compound is selected from the group consisting of:
2-(1-imidazolyl)-3,4-dihydro-7-amino-1(2H)-naphthalenone;
2-(1-imidazolyl)-3,4-dihydro-7-dimethylamino-1(2H)-naphthalenone;
2-(1-imidazolyl)-3,4-dihydro-7-acetylamino-1(2H)-naphthalenone;
2-(1-imidazolyl)-3,4-dihydro-7-methoxy-1(2H)-naphthalenone;
2-(1-imidazolyl)-3,4-dihydro-8-methoxy-1(2H)-naphthalenone;
2-(1-imidazolyl)-3,4-dihydro-5-bromo-6-methoxy-1(2H)-naphthalenone;
2-(1-imidazolyl)-3,4-dihydro-6-hydroxy-7-tert.butyl-1(2H)-naphthalenone;
2-(1-imidazolyl)-3,4-dihydro-5,7-dibromo-6-hydroxy-1(2H)-naphthalenone;
2-(1-imidazolyl)-3,4-dihydro-7-carboxy-1(2H)-naphthalenone;
2-(1-imidazolyl)-3,4-dihydro-5-bromo-7-carboxy-1(2H)-naphthalenone;
2-(1-imidazolyl)-3,4-dihydro-8-carboxy-1(2H)-naphthalenone;
2-(1-imidazolyl)-3,4-dihydro-7-methoxy-8-bromo-1(2H)-naphthalenone;
2-(1-imidazolyl)-3,4-dihydro-7-hydroxy-8-bromo-1(2H)-naphthalenone;
2-(1-imidazolyl)-3,4-dihydro-5-allyl-6-hydroxy-1(2H)-naphthalenone;
2-(1-imidazolyl)-3,4-dihydro-7-phenyl-1(2H)-naphthalenone;
2-(1-imidazolyl)-3,4-dihydro-3-methyl-1(2H)-naphthalenone;

2-(1-imidazolyl)-3,4-dihydro-3-carboxy-1(2H)-naphthalenone; and the pharmaceutically acceptable salts thereof.

9. A method according to claim 2, wherein said compound is selected from the group consisting of:
2-(1-imidazolyl)-1,2,3,4-tetrahydro-7-methoxy-1-naphthalenol;
2-(1-imidazolyl)-1,2,3,4-tetrahydro-7-carboxy-1-naphthalenol;
2-(1-imidazolyl)-1,2,3,4-tetrahydro-6-hydroxy-7-tert.butyl-1-naphthalenol;
2-(1-imidazolyl)-1,2,3,4-tetrahydro-5-bromo-6-hydroxy-1-naphthalenol;
2-(1-imidazolyl)-1,2,3,4-tetrahydro-8-carboxy-1-naphthalenol, both in the form of cis or trans isomer and of their mixture, and the pharmaceutically acceptable salts thereof.

10. A method according to claim 2, wherein said compound is selected from the group consisting of:
2-(1-imidazolyl)-5-methoxy-1-indanone;
2-(1-imidazolyl)-6-carboxy-1-indanone, and the pharmaceutically acceptable salts thereof.

11. A method according to claim 2, wherein said compound is
2-(1-imidazolyl)-3-methyl-1-indanone both in the form of cis or trans isomer and of their mixture, and the pharmaceutically acceptable salts thereof.

12. A method according to claim 2, wherein said compound is
2-(1-imidazolyl)-3,4-dihydro-5-bromo-6-hydroxy-1(2H)-naphthalenone, and the pharmaceutically acceptable salts thereof.

* * * * *